(12) United States Patent
Saltzman et al.

(10) Patent No.: US 7,030,097 B1
(45) Date of Patent: Apr. 18, 2006

(54) CONTROLLED NUCLEIC ACID DELIVERY SYSTEMS

(75) Inventors: William Mark Saltzman, Ithaca, NY (US); Dan Luo, Ithaca, NY (US); Hong Shen, Ithaca, NY (US); Kim Woodrow-Mumford, Tulare, CA (US); Nadya D. Belcheva, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/616,711

(22) Filed: Jul. 14, 2000

Related U.S. Application Data

(60) Provisional application No. 60/143,701, filed on Jul. 14, 1999.

(51) Int. Cl.
  *A01N 43/04* (2006.01)
  *A61K 31/70* (2006.01)
  *C12N 15/00* (2006.01)
  *C12N 15/09* (2006.01)
  *C12N 15/63* (2006.01)

(52) U.S. Cl. .................. 514/44; 435/455; 435/825; 435/320.1; 424/450

(58) Field of Classification Search .............. 435/320.1, 435/455, 825; 424/450; 514/44
  See application file for complete search history.

(56) References Cited

U.S. PATENT DOCUMENTS

| | | | |
|---|---|---|---|
| 4,900,556 A * | 2/1990 | Wheatley | 424/450 |
| 5,286,493 A * | 2/1994 | Oshlack | 424/468 |
| 5,445,609 A * | 8/1995 | Lattin et al. | 604/20 |
| 5,543,156 A * | 8/1996 | Roorda | 424/484 |
| 5,593,697 A | 1/1997 | Barr et al. | |
| 5,603,960 A | 2/1997 | O'Hagan et al. | |
| 5,635,216 A | 6/1997 | Thompson | |
| 5,741,521 A | 4/1998 | Knight et al. | |
| 5,763,157 A * | 6/1998 | Treml | 435/4 |
| 5,763,416 A | 6/1998 | Bonadio et al. | |
| 5,783,567 A | 7/1998 | Hedley et al. | |
| 5,792,477 A | 8/1998 | Rickey et al. | |
| 5,811,128 A | 9/1998 | Tice et al. | |
| 5,814,344 A | 9/1998 | Tice et al. | |
| 5,831,020 A * | 11/1998 | Cirovsky | |
| 5,853,763 A | 12/1998 | Tice et al. | |
| 5,869,103 A | 2/1999 | Yeh et al. | |
| 5,879,713 A | 3/1999 | Roth et al. | |
| 6,040,295 A * | 3/2000 | Rolland et al. | |
| 6,191,257 B1 * | 2/2001 | Ledley et al. | |
| 6,262,034 B1 * | 7/2001 | Mathiowitz et al. | 514/44 |
| 6,268,053 B1 * | 7/2001 | Woiszwillo | 428/402 |

(Continued)

FOREIGN PATENT DOCUMENTS

EP   0 827 741   * 3/1998

OTHER PUBLICATIONS

Abe et al., Enhanced Gene Transfer with Fusogenic Liposomes Containing Vesicular Stomatitis Virus G Glycoprotein, Jul. 1998, Journal of Virology, pp. 6159-6163.*

Yong et al., Controlled release of plasmid DNA, 1997, Journal of Controlled Release, vol. 47, pp. 123-134.*

Jones et al., "Poly(DL-lactide-co-glycolide)-encapsulated Plasmid DNA Elicits Systemic and Mucosal Antibody Responses to Encoded Protein After Oral Administration," *Vaccine* 15(8):814-817 (1997).

Saltzman et al., "Transport Rates of Protein in Porous Materials with Known Microgeometry," *Biophys. J.* 55:163-171 (1989).

Langer et al., "Polymers for the Sustained Release of Proteins and Other Macromolecules," *Nature* 263:797-800 (1976).

Mathiowitz et al., "Biologically Erodable Microspheres as Potential Oral Drug Delivery Systems," *Nature* 386:410-414 (1997).

(Continued)

*Primary Examiner*—Joseph Woitach
*Assistant Examiner*—Robert M. Kelly
(74) *Attorney, Agent, or Firm*—Nixon Peabody LLP

(57) ABSTRACT

One aspect of the present invention relates to a nucleic acid delivery system including a polymeric structure formed of a biocompatible polymer and a mixture comprising one or more nucleic acid molecules and a first co-dispersant, the mixture being contained within the polymeric structure, wherein the first co-dispersant is present in an amount effective to control diffusion of the one or more nucleic acid from the polymeric structure. Compositions including the nucleic acid delivery system and a pharmaceutically-acceptable carrier are disclosed. Methods of making the nucleic acid delivery system and their use in delivering nucleic acid into a patient and modifying gene expression in a target cell are also disclosed.

47 Claims, 12 Drawing Sheets

U.S. PATENT DOCUMENTS

| | | | |
|---|---|---|---|
| 6,309,669 B1 * | 10/2001 | Setterstrom | 424/486 |
| 6,312,727 B1 * | 11/2001 | Schacht et al. | |
| 6,312,731 B1 * | 11/2001 | Staas et al. | |
| 6,344,436 B1 * | 2/2002 | Smith et al. | |
| 6,375,944 B1 * | 4/2002 | Trinchieri et al. | |
| 6,429,199 B1 * | 8/2002 | Krieg | 514/44 |
| 6,509,146 B1 * | 1/2003 | Bronshtein | 435/1.3 |
| 6,667,294 B1 | 12/2003 | Jones et al. | |
| 6,743,444 B1 | 6/2004 | Jones et al. | |
| 2002/0065213 A1 * | 5/2002 | Debs | |

OTHER PUBLICATIONS

Labhasetwar et al., "A DNA Controlled-release Coating for Gene Transfer: Transfection in Skeletal and Cardiac Muscle," *Journal of Pharmaceutical Sciences* 87(11):1347-1350 (1998).

Krewson et al., "Stabilization of Nerve Growth Factor in Controlled Release Polymers and in Tissue," *J. Biomater. Sci. Polymer Edn.* 8(2):103-117 (1996).

* cited by examiner

US 7,030,097 B1

CONTROLLED NUCLEIC ACID DELIVERY SYSTEMS

This application claims benefit of U.S. Provisional Patent Application Ser. No. 60/143,701, filed Jul. 14, 1999, which is hereby incorporated by reference.

The present invention was made in part with funding from the National Institutes of Health Grant No. GM43873. The U.S. Government may have certain rights in this invention.

FIELD OF THE INVENTION

The present invention relates to controlled nucleic acid delivery systems and their use in delivering nucleic acid molecules to target cells, specifically for purposes of modifying target cell gene expression (i.e., gene therapy) and DNA vaccination.

BACKGROUND OF THE INVENTION

Directly injected DNA can express its encoded proteins and elicit specific immune responses in animals (Wolff et al., "Direct Gene Transfer Into Mouse Muscle in vivo," *Science* 47:1465–1468 (1990); Donnelly et al., "DNA Vaccines," *Annu. Rev. Immunol.* 15:617–648 (1997)). Most of the DNA delivery technologies reported so far have been focused on naked DNA delivery (as in DNA vaccination) and non-viral or viral vector mediated systems (Anderson, "Human Gene Therapy," *Nature* 392:25–30 (1998)). Clinical applications of viral-mediated systems have been delayed by safety issues such as mutagenic potential and immunogenicity (Crystal, "Transfer of Genes to Humans: Early Lessons and Obstacles to Success," *Science* 270:404–410 (1995) and Tripathy et al., "Immune Responses to Transgene-encoded Proteins Limit the Stability of Gene Expression After Injection of Replication-defective Adenovirus Vectors," *Nat. Med.* 2:545–550 (1996)). The generally poor efficiency of delivery and expression by non-viral systems remains one of the main limitations to the development of gene therapy and DNA vaccination (Thierry et al., "Characterization of Liposome-mediated Gene Delivery: Expression, Stability and Pharmacokinetics of Plasmid DNA," *Gene Ther.* 4:226–237 (1997) and Liu et al., "Cationic Liposome-mediated Intravenous Gene Delivery," *J. Biol. Chem.* 270:24864–24870 (1995)). Much attention is therefore being paid to the design of new formulations of DNA with various substances, such as lipid (Ishii et al., "Cationic Liposomes are a Strong Adjuvant for a DNA Vaccine of Human Immunodeficiency Virus Type 1," *AIDS Res. Hum. Retroviruses* 13:1421–1428 (1997)), polycation/polysaccharide (Erbacher et al., "Chitosan-based Vector/DNA Complexes for Gene Delivery: Biophysical Characteristics and Transfection Ability," *Pharm. Res.* 15:1332–1339 (1998)), peptide (Erbacher et al., "The Reduction of the Positive Charges of Polylysine by Partial Gluconoylation Increases the Transfection Efficiency of Polylysine/DNA Complexes," *Biochim. Biophys. Acta* 1324: 27–36 (1997)), peptoid (Murphy et al., "A Combinatorial Approach to the Discovery of Efficient Cationic Peptoid Reagents for Gene Delivery," *Proc. Natl. Acad. Sci. USA* 95:1517–1522 (1998)), gold particles (Fynan et al., "DNA Vaccines: Protective Immunizations by Parenteral, Mucosal, and Gene-Gun Inoculations," *Proc. Natl. Acad. Sci. USA* 90:11478–11482 (1993)), protein (Hart et al., "Gene Delivery and Expression Mediated by an Integrin-binding Peptide," *Gene Ther.* 2:552–554 (1995)), polymers (Katayose et al., "Water-soluble Polyion Complex Associates of DNA and Poly(ethylene glycol)-poly(L-lysine) Block Copolymer," *Bioconjug. Chem.* 8:702–707 (1997)), and other complexes (Kim et al., "A New Non-viral DNA Delivery Vector: The Terplex System," *J. Controlled Rel.* 53:175–182 (1998)). All of these systems deliver DNA as a bolus, without long-term sustained release.

Controlled release systems using biocompatible and/or biodegradable polymers provide an attractive alternative for long-term delivery of therapeutic agents (including DNA). There are many advantages of polymer-mediated controlled release systems over conventional delivery systems (Mahoney et al., "Controlled Release of Proteins to Tissue Transplants for the Treatment of Neurodegenerative Disorders," *J. Pharm. Sci.* 85:1276–1281 (1996)). These include: (i) therapeutic agents can be delivered to tissues in a sustained, continuous and predictable fashion; (ii) therapeutic agents are well protected before being released; (iii) site specific delivery (such as in brain) can be achieved by simple implantation or direct injection; and (iv) repeated drug administration is not necessary. Despite the fact that in recent years controlled release systems have been successfully employed to deliver proteins and other macromolecules (Cohen et al., "Controlled Delivery Systems for Proteins Based on Poly(lactic/glycolic acid) Microspheres," *Pharm. Res.* 8:713–720 (1991), Saltzman et al., "Transport Rates of Proteins in Porous Materials with Known Microgeometry," *Biophys. J.* 55:163–171 (1989); and Siegel et al., "Controlled Release of Polypeptides and Other Macromolecules," *Pharm. Res.* 1:2–10 (1984)), polymer-based DNA controlled release systems have not been fully explored. Several previous reports of DNA delivery using synthetic polymers have important limitations, such as limited range of DNA sizes and DNA dosages, reliance on non-FDA approved materials, difficulty in control of release rate (Mathiowitz et al., "Biologically Erodable Microspheres as Potential Oral Drug Delivery Systems," *Nature* 386:410–414 (1997); Jong et al., "Controlled Release of Plasmid DNA," *J. Controlled Rel.* 47:123–134 (1997); Labhasetwar et al., "A DNA Controlled-release Coating for Gene Transfer: Transfection in Skeletal and Cardiac Muscle," *J. Pharm. Sci.* 87:1347–1350 (1998); Wang et al., "Encapsulation of Plasmid DNA in Biodegradable Poly(D, L-lactic-co-glycolic acid) Microspheres as a Novel Approach for Immunogene Delivery," *J. Controlled Rel.* 57:9–18 (1999); and Ando et al., "PLGA Microspheres Containing Plasmid DNA: Preservation of Supercoiled DNA via Cryopreparation and Carbohydrate Stabilization," *J. Pharm. Sci.* 88:126–130 (1999)).

The present invention is directed to identifying factors responsible for modifying the controlled release rate of nucleic acid from biocompatible polymers, and otherwise overcoming the above-described deficiencies in the relevant art.

SUMMARY OF THE INVENTION

The present invention relates to a nucleic acid delivery system including a polymeric structure formed of a biocompatible polymer and a mixture comprising one or more nucleic acid molecules and a first co-dispersant, the mixture being contained within the polymeric structure, wherein the first co-dispersant is present in an amount effective to control diffusion of the one or more nucleic acid molecules from the polymeric structure. Compositions including the nucleic acid delivery system of the present invention and a pharmaceutically-acceptable carrier are also disclosed.

A further aspect of the present invention relates to a method of making a nucleic acid delivery system of the present invention. This method is carried out by providing a mixture including one or more nucleic acid molecules and a first co-dispersant, providing a biocompatible polymer, and then combining the mixture with the biocompatible polymer under conditions effective to form a polymeric structure in which the mixture is contained.

Another aspect of the present invention relates to a method of delivering a nucleic acid into a patient. This method is carried out by providing a nucleic acid delivery system of the present invention and administering the nucleic acid delivery system to the patient under conditions effective for delivery of the one or more nucleic acid molecules into the patient.

Yet another aspect of the present invention relates to a method of modifying gene expression in a target cell. This method is carried out by providing a nucleic acid delivery system of the present invention and introducing the nucleic acid delivery system into the environment of a target cell under conditions effective for delivery of the one or more nucleic acid molecules into the target cell, whereby the one or more nucleic acid molecules or their expressed products modify gene expression in the target cell.

By incorporating a co-dispersant into the polymeric structure along with the nucleic acid to be released over the course of time by the delivery system of the present invention, it is possible to control the release of nucleic acid from the polymeric structure. This provides a much better alternative than a single bolus injection and facilitates the continued incorporation of therapeutic nucleic acid molecules into target cells. Most current non-viral delivery systems have low efficiency, because toxic elements in the delivery system require that the exposure time is short. Controlled delivery systems of the present invention allow long-term release without repeated administration (i.e., long-term exposure), with fewer toxic agents, and an overall high efficiency. Moreover, nucleic acid molecules are protected by the polymeric structure before releasing and a single delivery system is adapted for simultaneous multiple encapsulation (i.e., for multiple treatments or vaccinations at the same time).

BRIEF DESCRIPTION OF THE DRAWINGS

In FIG. 1A, DNA release rate (mg/day), obtained from dividing net amount of released DNA by the length of two time points, is plotted at the time point 2. In FIG. 1B, cumulative DNA release in percentage.

FIGS. 4A–B illustrate the size distribution of DNA-containing microspheres formed of poly(D,L-lactide-co-glycolide) ("PLGA") 50:50, FIGS. 4C–D illustrate the size distribution of DNA-containing microspheres formed of poly(L-lactide) ("PLA")-300k, and FIGS. 4E–F illustrate the size distribution of DNA-containing microspheres formed of PLA-2k.

FIG. 5A illustrates cumulative DNA release in percentage, for DNA-containing microspheres formed of PLGA 50:50 (□), PLA-2k (Δ), and PLA-300k (◇). Average and standard deviations were calculated from triplicates. FIG. 5B illustrates DNA release rate in μg/mg PLGA/day. PLGA microspheres are loaded with 0.5% (□), 0.3% (◇), 0.15% (Δ), and 0.01% (x) DNA (wt/wt). Insets have the same legends as the main figures.

DETAILED DESCRIPTION OF THE INVENTION

Figure 1A:
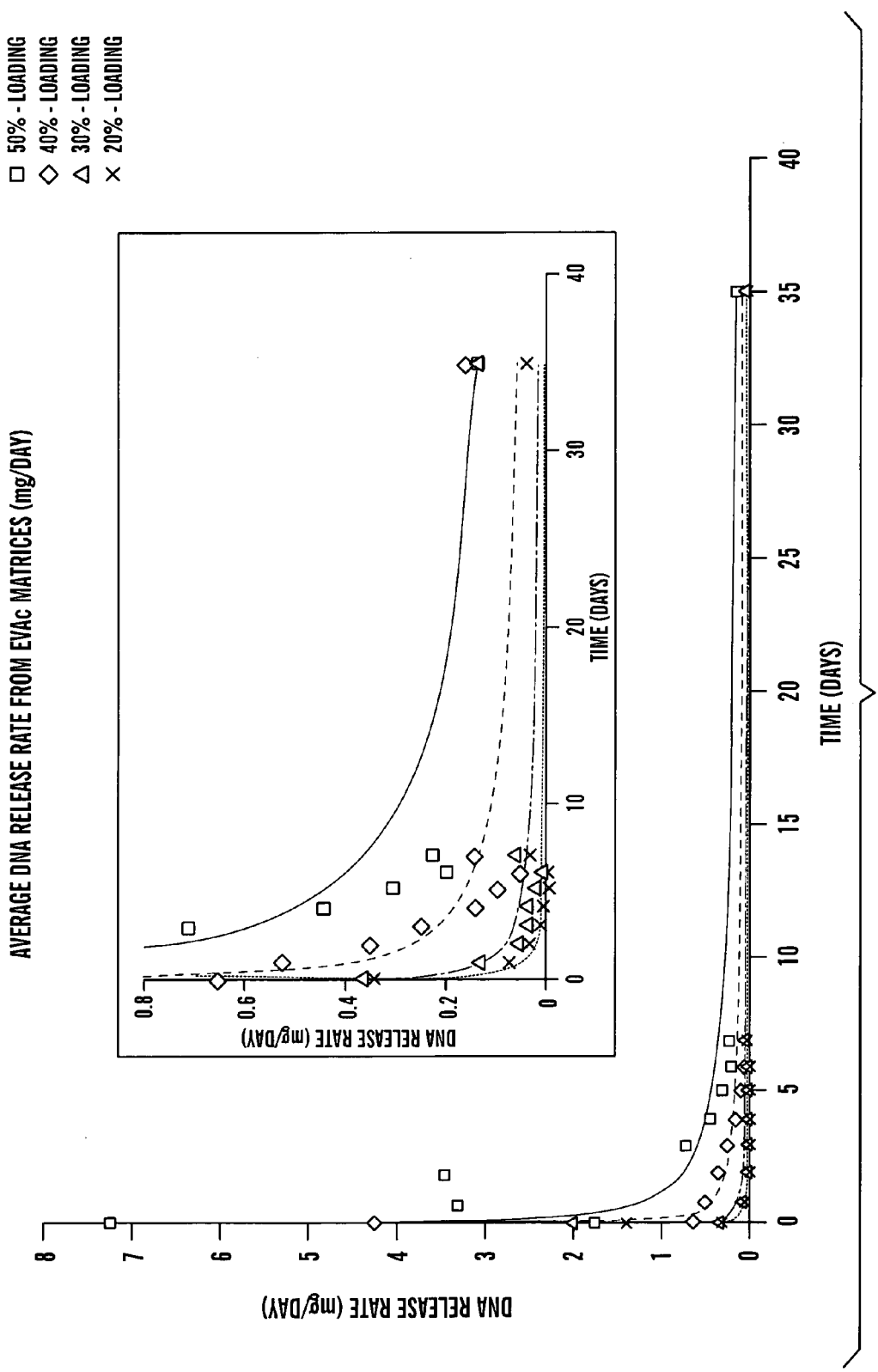
FIGS. 1A–B are graphs depicting the controlled DNA release from poly(ethylene-co-vinyl acetate) ("EVAc") matrices. Each data point is the average of quadruplicate EVAc discs. The symbols represent different amounts of DNA (weight percentage) encapsulated in EVAc matrices: 50% (□), 40% (◇), 30% (Δ) and 20% (x).

One aspect of the present invention relates to a nucleic acid delivery system including a polymeric structure formed of a biocompatible polymer and a mixture which includes one or more nucleic acid molecules and a first co-dispersant. The mixture is contained within the polymeric structure and the first co-dispersant is present in an amount effective to control diffusion of the nucleic acid from the polymeric structure.

The polymeric structure can be in the form of any suitably shaped polymeric matrix or a polymeric microsphere. The particular configuration of the polymeric structure may depend, at least in part, upon the type of biocompatible polymer which is utilized and the mode by which it is prepared. For example, certain biocompatible polymers can be used to form a single, substantially homogeneous body or matrix of the polymeric material. In contrast, other biocompatible polymers can be used to form a plurality of microspheric structures of the polymeric material.

Suitable biocompatible polymers can be obtained from commercial sources or can be prepared by known methods. For example, polymers of lactic and glycolic acid can be generated as described in U.S. Pat. No. 4,293,539 to Ludwig et al., which is hereby incorporated by reference. Such polymers are also commercially available from Aldrich. Alternatively, or in addition, the biocompatible polymer can include poly(ethylene-co-vinyl acetate), poly-L-lactide, poly-D-lactide, polyglycolide, poly(lactide-co-glycolide), polyanhydride, polyorthoester, polycaprolactone, polyphosphazene, proteinaceous polymer, polyester, polyorthoester, silicone, or combinations thereof.

Preferred DNA delivery systems of the present invention include poly(ethylene-co-vinyl acetate) and co-polymers of D- or L-lactic acid and glycolic acid wherein the weight ratio of lactic acid to glycolic acid is no more than about 10:1, more preferably 5:1. Since polymers of lactic acid take at least about one year to degrade in vivo, their use is desirable under circumstances where a lengthy degradation rate is practical for a particular therapeutic regimen.

Depending upon the particular mode of administration for the nucleic acid delivery system, the polymeric structure can be appropriately sized. For example, for implantable nucleic acid delivery systems, the polymeric structure is preferably a matrix which is less than about 10 cm in length, more preferably between about 10 µm to about 10 mm in length. In contrast, for alternative routes of introducing the nucleic acid delivery systems (i.e., into a patient), the polymeric structure is preferably a microsphere which is less than about 10 µm in length, more preferably about 0.5 µm to about 5 µm in length. By length, it is intended that the polymeric structure is measured along its longest axis.

The one or more nucleic acid molecules can be the same or different. For example, the one or more nucleic acid molecules can be (at least) two nucleic acid molecules which are to be delivered into a target cell. When two distinct nucleic acid molecules are delivered via the delivery system of the present invention, the two nucleic acid molecules can be used for a single therapeutic purpose or for multiple therapeutic purposes. The one or more nucleic acid molecules can be either DNA or RNA.

Each of the one or more nucleic acid molecules can be inserted into a heterologous expression vector and/or conjugated to or associated with other components for delivery of the one or more nucleic acid molecules into target cells. In certain embodiments, stable transformation of the target cell is desired.

The target cell is typically, although not exclusively, a mammalian target cell. The target cell can be either in vitro or in vivo.

Each of the one or more nucleic acid molecules is preferably a transgene which includes a promoter region and other appropriate transcription and translation control sequences known in the art (e.g., 3' polyadenylation signals). When the target cell is a mammalian cell, the promoter region used to construct the nucleic acid molecule should be appropriate for the particular mammalian target cell. Promoters vary in their "strength" (i.e., their ability to promote transcription). For the purposes of expressing a cloned transgene, it is often desirable to use strong promoters in order to obtain a high level of transcription and, hence, expression of the gene. Suitable promoters include, without limitation, SV40, MMTV, metallothionein-1, adenovirus Ela, CMV early, immunoglobulin heavy chain promoter and enhancer, and RSV-LTR.

A DNA molecule coding for a desired RNA molecule or protein or polypeptide can be ligated readily to its appropriate promoter and other transcription and translation control sequences, in either a sense or an antisense orientation, using well known molecular cloning techniques (Sambrook et al., *Molecular Cloning: A Laboratory Manual*, Second Edition, Cold Spring Harbor Press, NY (1989), which is hereby incorporated by reference). The resulting transgene can be designed to express either antisense RNA, an untranslatable mRNA transcript, or a translatable mRNA transcript and, therefore, a protein or polypeptide.

To prepare a transgene capable of expressing an antisense RNA molecule, the DNA molecule coding for a particular RNA molecule or protein or polypeptide is ligated to the promoter and other regulatory sequences in reverse orientation. Ligation of DNA molecules in reverse orientation can be performed according to known techniques which are standard in the art. Upon transcription of the DNA molecule, the resulting RNA molecule will be complementary to the mRNA transcript coding for the actual protein or polypeptide product. Such antisense nucleic acid molecules may be used in gene therapy to treat or prevent various disorders. For a discussion of the regulation of gene expression using antisense genes, see Weintraub et al., *Reviews-Trends in Genetics*, 1(1) (1986), which is hereby incorporated by reference.

To prepare a transgene capable of expressing an untranslatable RNA molecule, the DNA molecule coding for a desired RNA molecule is modified to provide for altered translation stop and/or start signals as is known in the art. When expressed, the untranslatable RNA molecule will not be capable of translation into an encoded protein or polypeptide. Such untranslatable RNA molecules can also be used in gene therapy to treat or prevent various disorders.

By way of example, suitable expression vectors for mammalian cell transformation include, without limitation, retroviral vectors and other RNA virus vectors, adenoviral vectors and other DNA virus vectors, and plasmid constructs. While any number of suitable expression vectors can be utilized in the nucleic acid delivery system of the present invention, non-infective expression vectors (i.e., plasmid constructs) are preferred. Release of such expression vectors from the nucleic acid delivery system of the present invention allows for the in vivo transfection of target cells and subsequent expression of the heterologous nucleic acid molecule.

Adenoviral vectors which have been modified (i.e., rendered replication-deficient) to form infective transformation systems can be used to deliver a DNA molecule into a host cell. Adenoviruses are double-stranded DNA viruses which can be stably incorporated into the host's cellular DNA. Thus, the one or more nucleic acid molecules can be a DNA molecule which is inserted into a heterologous adenovirus express vector. Adenovirus expression vectors can be readily prepared and utilized given the disclosure provided in Berkner, *Biotechniques* 6:616–627 (1988), Rosenfeld et al., *Science* 252:431–434 (1991), WO 93/07283, WO 93/06223, and WO 93/07282, which are hereby incorporated by reference. The use of adeno-associated viral gene delivery vehicles in vitro is described in Chatterjee et al., *Science* 258:1485–1488 (1992); Walsh et al., *Proc. Nat'l. Acad. Sci.* 89:7257–7261 (1992); Walsh et al., *J. Clin Invest.* 94:1440–1448 (1994); Flotte et al., *J. Biol. Chem.* 268: 3781–3790 (1993); Ponnazhagan et al., *J. Exp. Med.* 179: 733–738 (1994); Miller et al., *Proc. Nat'l Acad. Sci.* 91:10183–10187 (1994); Einerhand et al., *Gene Ther.* 2:336–343 (1995); Luo et al., *Exp. Hematol.* 23:1261–1267 (1995); and Zhou et al., *Gene Ther.* 3:223–229 (1996), which are hereby incorporated by reference. In vivo use of these vehicles is described in Flotte et al., *Proc. Nat'l Acad. Sci.* 90:10613–10617 (1993); and Kaplitt et al., *Nature Genet.* 8:148–153 (1994), which are hereby incorporated by reference. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; and U.S. Pat. No. 5,885,808 to Spooner et al.; and U.S. Pat. No. 5,871,727 to Curiel, which are hereby incorporated by reference).

Retroviral vectors which have been modified (i.e., rendered replication-deficient) to form infective transformation systems can be used to deliver an RNA molecule into a host cell. Retroviruses are RNA viruses which can replicate and integrate into a host cell genome through a DNA intermediate, which is prepared by a viral reverse transcriptase. The DNA intermediate, or provirus, can be stably incorporated into the host cellular DNA. Thus, the one or more nucleic acid molecules can be an RNA molecule which is inserted into a heterologous retroviral expression vector. Exemplary retroviral vectors and packaging cell lines which express them are disclosed in U.S. Pat. No. 5,849,586 to Kriegler et al., U.S. Pat. No. 6,013,517 to Respass et al., and U.S. Pat. No. 6,025,192 to Beach et al., which are hereby incorporated by reference. The RNA molecule, when reverse transcribed, yields a DNA molecule that can encode the RNA or protein or polypeptide as described above.

Although the above described infective transformation expression systems can be employed, it is often desirable to use smaller plasmid expression vectors, which due to their smaller size can be expected to diffuse from the polymeric structure at typically faster rates than the larger infective transformation systems. Plasmid constructs containing suitable promoters, suitable transcription and translation regulatory regions, and suitable linkers (with appropriate restriction sites) can be prepared for subsequent introduction of the one or more nucleic acid molecules according to techniques which are well known in the art. For other reasons, including concerns of replication-deficient infective transformation systems reacquiring an ability to replicate, such plasmid constructs may also be more desirable for in vivo use.

Regardless of the type of nucleic acid, the one or more nucleic acid molecules is intended to be taken up by a target cell. Thus, the nucleic acid delivery system also includes a cellular uptake agent. The cellular uptake agent can be independent of the one or more nucleic acid molecules or coupled individually to each of them.

Suitable independent cellular uptake agents which promote absorption of the one or more nucleic acid molecules by the target cell include TRANSFAST™ (Promega, Inc., Madison, Wis.) and SUPERFECT™ (Qiagen Inc., Valencia, Calif.). TRANSFAST™ is comprised of the synthetic cation lipid (+)-N,N[bis(2-hydroxyethyl)-N-methyl-N-[2,3-di(tetradecanoyloxy)propyl] ammonium] iodide and the neutral lipid L-dieoyl phosphatidylethanolamine. It is supplied as a dried lipid film which forms multilamellar vesicles upon hydration with water.

Alternatively the cellular uptake agent can be covalently or non-covalently attached to the one or more nucleic acid molecules. Suitable cellular uptake agents which can be coupled individually to the one or more nucleic acid molecules include various receptor binding ligands which are capable of recognizing and binding to an appropriate receptor on the target cell surface. Numerous molecules that bind specific receptors have been identified and are suitable for use in the present invention. Such molecules include growth factors, cytokines, and antibodies. Many growth factors and families of growth factors share structural and functional features and may be used in the present invention. One such family of growth factors specifically binds to heparin. The ability of heparin-binding growth factors to interact with heparin appears in general to be a reflection of a physiologically relevant interaction occurring in vivo between these factors and heparin sulfate proteoglycan molecules, which are found on the surface of cells and in extracellular matrix. Heparin-binding growth factors include fibroblast growth factors FGF-1 through FGF-9, vascular endothelial growth factor (VEGF), and heparin binding-epidermal growth factor (HBEGF). Antibodies that are specific to cell surface molecules expressed by a selected cell type are readily generated as monoclonals or polyclonal antisera. Many such antibodies are available (e.g., from American Type Culture Collection, Rockville, Md.). Other growth factors, such as PDGF (platelet-derived growth factor), EGF (epidermal growth factor), TGF-α (tumor growth factor), TGF-β, IGF-I (insulin-like growth factor), and IGF-II also bind to specific identified receptors on cell surfaces and may be used in the present invention. Cytokines, including interleukins, CSFs (colony stimulating factors), and interferons, have specific receptors, which are mostly found on hematopoeitic cells, and may be used as described herein. Suitable receptor binding ligands are continually being identified and their use in connection with the present invention is similarly contemplated.

Fragments of such ligands may also be used within the present invention, so long as the fragments retain the ability to bind to the appropriate target cell surface molecule. Likewise, ligands with substitutions or other alterations, but which retain binding ability, may also be used.

Covalent attachment of the cellular uptake agent to the one or more nucleic acid molecules can be achieved by UV crosslinking (Hung et al., "Characterization of Topoisomerase II-DNA Interaction and Identification of a DNA-binding Domain by Ultraviolet Laser Crosslinking," *FEBS Lett.* 380(1–2):127–32 (1996), which is hereby incorporated by reference) or chemical crosslinking with crosslinkers such as Psoralen (Sastry et al., "Cross-linking of DNA-binding Proteins to DNA with Psoralen and Psoralen Furanside Monoadducts: Comparison of Action Spectra with DNA—DNA Cross-linking," *J. Biol. Chem.* 272(6):3715–23 (1997); Perkins et al., "Psoralen Photocross-linking by Triplex-forming Oligonucleotides at Multiple Sites in the Human Rhodopsin Gene," *Biochemistry* 38(39):12850–9 (1999), which are hereby incorporated by reference).

Non-covalent attachment of the cellular uptake agent to the one or more nucleic acid molecules can be achieved by exploiting electrostatic or hydrophobic interactions. By way of example, one suitable approach is the BANG technology (see Luo, "Novel Crosslinking Technologies to Assess Protein-DNA Binding and DNA—DNA Complexes for Gene Delivery and Expression," in Molecular, Cellular, and Developmental Biology Program, The Ohio State University: Columbus (1997), which is hereby incorporated by reference).

Alternatively, the cellular uptake agent can be attached to the one or more nucleic acid molecules via a chemical or peptide linker that links a receptor binding ligand or fragment thereof directly to a nucleic acid molecule or indirectly via a nucleic acid binding agent (such as poly-L-lysine). Suitable linkers and their use are described, for example, in U.S. Pat. No. 6,037,329 to Baird et al., which is hereby incorporated by reference.

When the one or more nucleic acid molecules is a DNA molecule, each is provided with a nucleus translocation agent, which enables the DNA molecule to pass from the cytoplasm into the nucleus of the target cell. The nucleus translocation agent can be coupled individually, and either covalently or non-covalently as described above, to each of the one or more nucleic acid molecules.

Suitable nucleus translocation agents are nuclear translocation sequences ("NTS"), which are polypeptide sequences in a protein that are required for translocation of that protein into a cell nucleus. Examples of NTSs are set forth in Table 1 below. Comparison with known NTSs, and if necessary testing of candidate sequences, should permit those of skill in the art to readily identify other amino acid sequences that function as NTSs. The NTS may be derived from another polypeptide, or it may be derived from another region in the same polypeptide.

TABLE 1

Nuclear Translocation Sequences

| Source | Sequence | SEQ. ID. No. |
| --- | --- | --- |
| SV40 large T | Pro$^{126}$LysLysArgLysValGlu | 1 |
| Polyoma large T | Pro$^{279}$ProLysLysAlaArgGluVal | 2 |
| Human c-Myc | Pro$^{120}$AlaAlaLysArgValLysLeuAsp | 3 |
| Adenovirus E1A | Lys$^{281}$ArgProArgPro | 4 |
| Yeast mat alpha 2 | Lys$^{3}$IleProIleLys | 5 |
| c-Erb-A | Gly$^{22}$LysArgLysArgLysSer | 6 |
| c-Erb-B | Ser$^{127}$LysArgValAlaLysArgLysLeu | 7 |
| c-Erb-C | Ser$^{181}$HisTrpLysGlnLysArgLysPhe | 8 |
| c-Myb | Pro$^{521}$LeuLeuLysLysIleLysGln | 9 |
| p53 | Pro$^{316}$GlnProLysLysLysPro Pro$^{277}$GlnProLysLysLysPro | 10 |
| Nucleolin | GlyLysArgLysLysGluMetThrLys-GlnLysGluValPro | 11 |
| HIV Tat | Gly$^{48}$ArgLysLysArgArgGlnArgArg-ArgAlaPro | 12 |
| FGF-1 | AsnTyrLysLysProLysLeu | 13 |
| FGF-2 | HisPheLysAspProLysArg | 14 |
| FGF-3 | AlaProArgArgArgLysLeu | 15 |
| FGF-4 | IleLysArgLeuArgArg | 16 |
| FGF-5 | GlyArgArg | 17 |
| FGF-6 | IleLysArgGlnArgArg | 18 |
| FGF-7 | IleArgValArgArg | 19 |

Xaa$^{n}$ denotes amino acid position in source protein

All presently identified members of the FGF family of peptides contain an NTS (see WO 91/15229, which is hereby incorporated by reference). A typical consensus NTS sequence contains an amino-terminal proline or glycine followed by at least three basic residues in a array of seven to nine amino acids (Dang et al., *J. Biol. Chem.* 264:18019–18023 (1989); Dang et al., *Mol. Cell. Biol.* 8:4049–4058 (1988), which are hereby incorporated by reference).

To regulate delivery of the one or more nucleic acid molecules from the nucleic acid delivery system in a controlled manner, the first co-dispersant is included in the mixture contained in the polymeric structure. The first co-dispersant is preferably an inert compound which does not interact with the one or more nucleic acid molecules but, instead, by its presence, moderates diffusion of the one or more nucleic acid molecules from the polymeric structure.

Suitable first co-dispersants include, without limitation, HS-DNA, random or non-coding DNA having a molecular weight of about 100 kDa to about 2000 kDa, more preferably about 200 kDa to about 1000 kDa, DNase-free filler such as Ficoll, DNase-free bulk protein such as DNase free BSA, DNase free peptide such as cell permeable peptide (Kanzaki et al., "Activation of the Calcium-permeable Cation Channel CD20 by Alpha Subunits of the Gi Protein," *J. Biol. Chem.* 272(23):14733–9 (1997), which is hereby incorporated by reference), glycoproteins such as viral glycoproteins (Abe et al., "Enhanced Gene Transfer with Fusogenic Liposomes Containing Vesicular Stomatitis Virus G Glycoprotein," *J. Virol.* 72(7):6159–63 (1998), which is hereby incorporated by reference), peptide-nucleic acids such as specific synthesized PNA (Scarfi et al., "Synthesis, Uptake, and Intracellular Metabolism of a Hydrophobic Tetrapeptide-peptide Nucleic Acid (PNA)-biotin Molecule," *Biochem. Biophys. Res. Commun.* 236(2):323–6 (1997), which is hereby incorporated by reference), and combinations thereof.

The weight ratio of the one or more nucleic acid molecules to the first co-dispersant is preferably about 0.00011–1:1, more preferably 0.0011–0.1:1, most preferably about 0.01–0.05:1.

In addition, the mixture can also include a second co-dispersant which stabilizes the DNA. Suitable second co-dispersants include cationic polymers such as poly-L-lysine ("PLL") and its conjugates (e.g., PLL-gal4-invasin) and copolymers (e.g., polyethylene glycol-PLL block copolymer), polyethyleneimine, diethylaminoethyl-dextran, cationic dendritic polymers, and combinations thereof; DNA binding proteins such as hi stones, histone-1 derived peptide, cationic polypeptides, protamines, spermine, spermidines, and combinations thereof; and DNase inhibitors such as DMI-2 (Ross, G. F., et al., Enhanced Reporter Gene Expression in Cells Transfected in the Presence of DMI-2, an Acid Nuclease Inhibitor," *Gene Ther* 5(9):1244–50 (1998), which is hereby incorporated by reference).

Alternatively, the one or more nucleic acid molecules can be conjugated nucleic acid molecules of the type described in U.S. Pat. No. 6,037,329 to Baird et al., which is hereby incorporated by reference. Conjugated nucleic acid molecules of the type described by Baird et al. include a receptor binding ligand which is a polypeptide reactive with a cell surface receptor on the target cell, a nucleic acid binding domain that binds to a nucleic acid to be delivered into a target cell, and the nucleic acid. With such conjugated nucleic acid molecules, it is possible to obviate the need for inserting the heterologous DNA or RNA molecule into an infective expression vector of the type described above.

A further aspect of the present invention relates to a method of making a nucleic acid delivery system of the present invention. Basically, this method is carried out by providing a mixture including one or more nucleic acid molecules and a first co-dispersant, providing a biocompatible polymer, and then combining the mixture with the biocompatible polymer under conditions effective to form a polymeric structure in which the mixture is contained.

Depending upon the types of biocompatible polymers employed and the desired polymeric structure to be formed, the conditions employed may be varied as is well known to those of skill in the art.

For example, according to one approach, a polymeric matrix can be formed by dissolving a suitable amount of EVAc in methylene chloride (i.e., 100 mg/ml), adding lyophilized DNA powder (containing a mixture of inert HS-DNA and expression vector DNA), briefly vortexing the mixture, and immediately pouring the mixture into a dry-ice chilled mold. The mixture in the mold can then be chilled quickly, followed by evaporation of methylene chloride. By varying the size and shape of the mold or modifying the matrix configuration after methylene chloride evaporation, the resulting DNA-EVAc matrix can be appropriately sized and configured.

According to another approach, a modification of the double emulsion (water/oil/water) solvent evaporation technique (Jones et al., "Poly(DL-lactide-co-glycolide)-encapsulated Plasmid DNA Elicits Systemic and Mucosal Antibody Responses to Encoded Protein After Oral Administration," *Vaccine* 15:814–817 (1997); Krewson et al., "Stabilization of Nerve Growth Factor in Controlled Release Polymers and in Tissue," *J. Biomater. Sci. Polym. Ed.* 8:103–117 (1996), which is hereby incorporated by reference), can be employed. Briefly, a suitable amount of PLGA ($M_n$=54,100, Birmingham Polymers, Birmingham, Ala.) or PLA ($M_n$=2000, and 300,000, Polysciences Inc. Warrington, Pa.) can be dissolved in methylene chloride (100 mg/ml). A mixture of inert DNA and expression vector DNA can be lyophilized and then used to prepare a DNA solution. While vortexing the polymer solution, the DNA solution is added drop-wise and then sonication is performed in crushed ice for about 10 seconds to achieve a homogeneous first emulsion. To the first emulsion, aqueous 1.0% polyvinyl alcohol ("PVA") (25000 $M_w$, 88 mol % hydrolyzed, Polysciences) is added slowly on ice. Sonication is then repeated for another 10 seconds to form a second emulsion. Finally, the second emulsion is added to 0.3% PVA solution while vigorously stirring, and the mixture is kept under continuous stirring at room temperature until microspheres have formed (i.e., about 3 hours). Centrifugation can be performed at about 3000 rpm at 4° C. for 10 minutes to collect microspheres. Collected microspheres can be washed and lyophilized using standard procedures.

Having prepared the nucleic acid delivery system, it can be administered alone or it can be further combined with a pharmaceutically-acceptable carrier to produce a pharmaceutical composition of the present invention.

The nucleic acid delivery system, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes, such as, that of the nose, throat, and bronchial tubes (i.e., inhalation).

For most therapeutic purposes, the nucleic acid delivery system can be administered orally as a solid or as a suspension in liquid form, via injection as a suspension in liquid form, via inhalation of a nebulized suspension, or via implantation of the nucleic acid delivery system in solid form.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the nucleic acid delivery system in suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

For implantation, the polymeric structure can be implanted directly into tissues (i.e., containing the target cells) with or without the presence of other pharmaceutically-acceptable carriers, excipients, or stabilizers.

A further aspect of the present invention relates to a method of delivering a nucleic acid molecule into a patient which is carried out by providing a nucleic acid delivery system of the present invention and administering the nucleic acid delivery system to the patient under conditions effective for delivery of the one or more nucleic acid molecules into the patient.

By delivering the one or more nucleic acid molecules to the patient, where the nucleic acid molecules are taken up by target cells, it is possible to modify gene expression within the target cells. Thus, another aspect of the present invention relates to a method of modifying gene expression in a target cell, which is carried out by providing a nucleic acid delivery system of the present invention and introducing the nucleic acid delivery system into the environment of a target cell under conditions effective for delivery of the one or more DNA molecules into the target cell, whereby the one or more nucleic acid molecules or their expressed products modify gene expression in the target cell.

By modify gene expression, it is intended to encompass either up- or down-regulation of a target cell gene, interference with translation of a target cell mRNA transcript, or expression of a heterologous protein or polypeptide. As noted above, introduction or expression of RNA molecules (e.g., translatable, untranslatable, or antisense) can modify the expression of target cell proteins or polypeptides or result in expression of a heterologous protein or polypeptide. Proteins or polypeptides can, in turn, up- or down-regulate another gene in the target cell. Regardless of the strategy employed, controlled release of nucleic acid by the nucleic acid delivery system of the present invention, followed by uptake of the nucleic acid by a target cell, provides for the modification of the gene expression of the target cell.

To enhance the opportunity for target cell uptake of the one or more nucleic acid molecules released by the nucleic acid delivery system, the nucleic acid delivery system is introduced into the environment of the target cell. When the target cell exists in an in vitro cell culture, the environment is the cell culture itself. When the target cell exists in vivo, the environment can be either the body of the patient or, more specifically, a particular tissue in which the target cells reside.

EXAMPLES

The following examples are provided to illustrate embodiments of the present invention but are by no means intended to limit its scope.

Materials and Methods

Microsphere Entrapment Efficiency Analysis:

Microspheres were evaluated for DNA content using the following extraction procedure. Briefly, 30 mg of microspheres were dissolved in a glass scintillation vial with 1 ml of methylene chloride. To extract the DNA from the organic solution, Milli-Q water was added to the oil phase and vortexed vigorously for 1 minute before centrifuge at 1000 rpm for 10 minutes. The aqueous phase was collected carefully. Three extractions were performed with a total collection of 1.5 ml of aqueous fraction. Each microsphere formulation was analyzed in duplicate. Blank, DNA-free microspheres and pure DNA were also subjected to the same extraction procedure as controls. The extracted DNA content was analyzed by a DNA-specific fluoroassay.

DNA Assays:

DNA concentration was determined using a PicoGreen ($E_x$=480 nm, $E_m$=520 nm) dsDNA quantitation Kit (Molecular Probes, Inc., Eugene, Oreg.). A standard curve of λ DNA was constructed at the same time, and DNA concentrations were determined from unknown samples by comparison to the standard curve. The limit of detection for this assay was 50 pg/ml.

Scanning Electron Microscopy (SEM):

Microsphere morphology was analyzed by scanning electron microscopy (Steroscan 440, Leica Cambridge, Ltd.). A monolayer of dry microspheres was mounted on an aluminum stub using double-sided carbon tape. The sample was coated with a 10 nm thick palladium/gold (60:40) film using a sputter coater (Desk II, Denton Vacuum, Inc.). The coated samples were examined using an electron acceleration voltage of 5–10 keV. Size distribution and average particle diameter were determined by analyzing 5–10 images, representing >2000 particles, using the freeware program NIH-Image (NIH-Image, which was written by Wayne Rasband, is available by anonymous FTP from zippy.nimh.nih.gov).

Electrophoresis:

Gel electrophoresis was performed at a constant 100 volts. DNA was separated in 1% of agarose gel and stained for 0.5 hr in SYBR Green II solution (Molecular Probes, Inc., Eugene, Oreg.). DNA bands were quantified using the Multi-Analysis program (Bio-Rad Laboratory, Hercules, Calif.).

Controlled Release of DNA into PBS:

EVAc matrices (quadruplicates) were incubated in 4 ml of phosphate-buffered saline (PBS) containing 0.02% gentamicin sulfate for up to 30 days at 37° C. with gentle shaking. At a predetermined time point, the entire PBS solution was replaced with fresh PBS. An aliquot of pure non-encapsulated DNA was also incubated in PBS as controls; samples were removed for evaluation of DNA degradation at the same time intervals.

Microspheres were incubated in 0.3 ml of PBS containing 0.02% gentamicin sulfate for up to 30 days at 37° C. with gentle shaking. Periodically, 0.2 ml of buffer was collected after centrifugation and replaced with 0.2 ml of fresh buffer. Blank microspheres, treated identically, were used as controls.

PCR and Transfection Assay:

PCR reactions were performed using the GeneAmp PCR System 2400 (Perkin Elmer Applied Biosystems) according to standard PCR protocols. Briefly, 3 ng of template DNA pGFP-C2 (Promega, Madison, Wis.) was amplified with 0.5 µM of the following primers:

BGFPUP (SEQ. ID. No. 20):

CTGATTCTGT GGATAACCGT ATT         23

BGFPDOWN (SEQ. ID. No. 21):

TGGAACAACA CTCAACCCTA TCT         23

An expected single 1.9 kb band was detected. CHO cells (American Type Culture Collection, Rockville, Md.) were transfected by FUGENE 6 (Boehringer Mannheim, Indianapolis, Ind.) with 1 µg of DNA. GFP expressions were visualized by fluorescence microscopy 24 hours post-transfection.

Example 1

Fabrication and Evaluation of DNA-Encapsulated EVAc Matrices

One hundred mg of HS-DNA (10 mg/ml) were lyophilized overnight. The dry powder was ground to a size <100 µm before incorporation into EVAc matrices. The encapsulation procedures were modified based on a previously published protein encapsulation method (Beaty et al., "Controlled Growth Factor Delivery Induces Differential Neurite Outgrowth in Three-dimensional Cell Cultures," *J. of Controlled Rel.* 24:15–23 (1993), which is hereby incorporated by reference). Briefly, 100 mg of EVAc (Dupont, Wilmington, Del.) was dissolved in 1 ml of methylene chloride. After adding DNA powder, the mixture was vortexed briefly and immediately poured into a dry ice-chilled mold. The mixture in the mold was then quickly chilled and subsequently removed and placed in the −20° C. freezer. Methylene chloride was evaporated for 2 days and then for another 2 days under vacuum at room temperature. The resulting DNA-EVAc slabs were cut into 4 blocks weighing about 40 mg. No detectable degradation of pure, non-encapsulated HS-DNA was found during continuous incubation in PBS at 37° C. for up to 35 days.

Figure 1B:
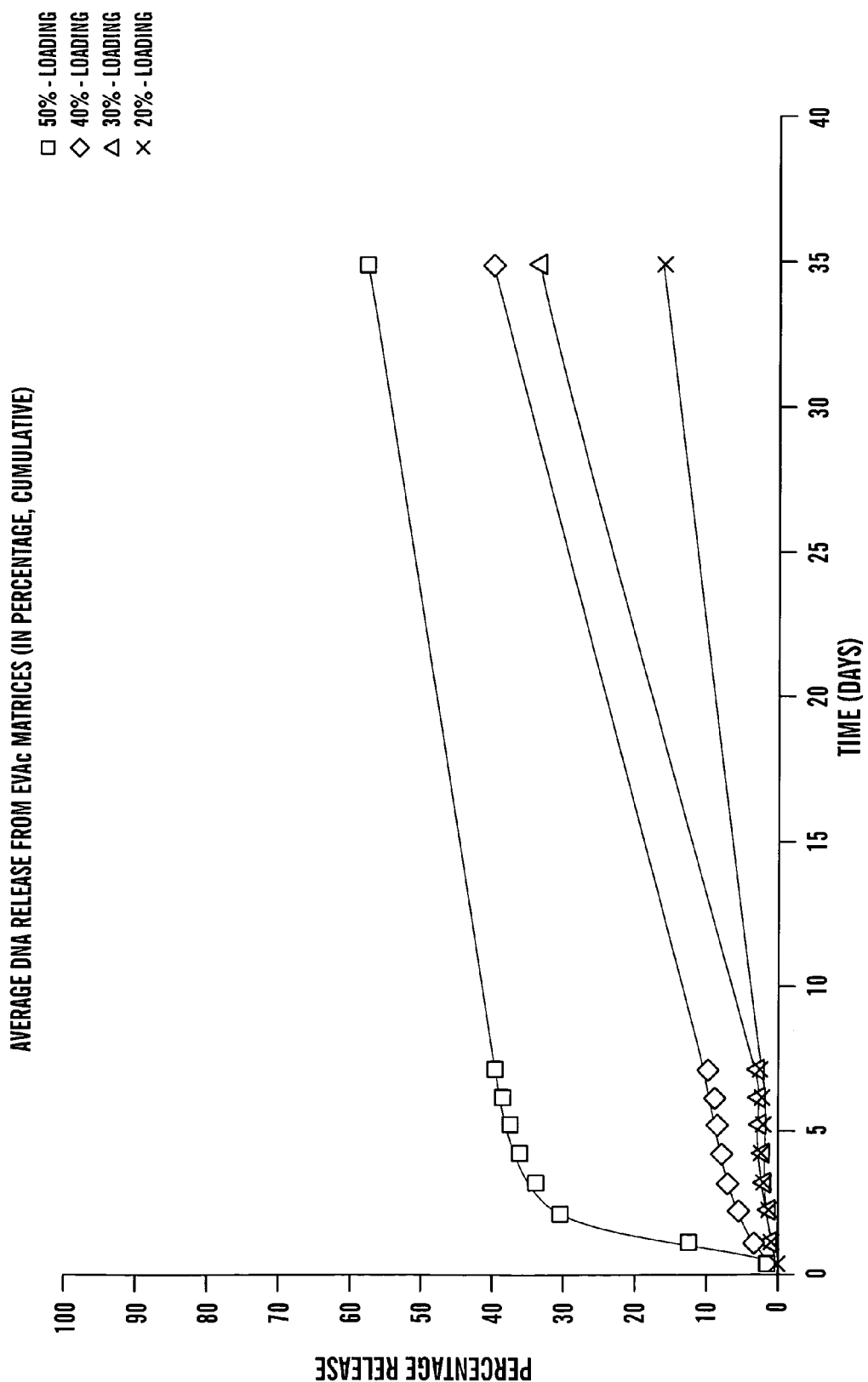

HS-DNA was employed as a model system for evaluating delivery of linear, double-stranded DNA of small size (600 bp). DNA was continuously released from all DNA-EVAc matrices over the duration of the experiment (>1 month) (FIGS. 1A–B). Among different EVAc matrices, a similar bi-phasic behavior of DNA release was observed: an initial burst of release (phase I) and a period of slow, but continuous, release (phase II). Release rates during phase I increased as the percentage of DNA initially in the matrix increased, whereas release rates during phase II were similar among different loaded matrices (FIG. 1A inset). The cumulative percentage of DNA released was also affected by the EVAc loading capacity (FIG. 1B). After two weeks of incubation in the buffered solution, about ½ of the encapsulated DNA was released from 50% loaded EVAc while only 20%, 10%, and 5% of the payload was released from 40%, 30%, and 20% loaded matrices, respectively.

Figure 2:
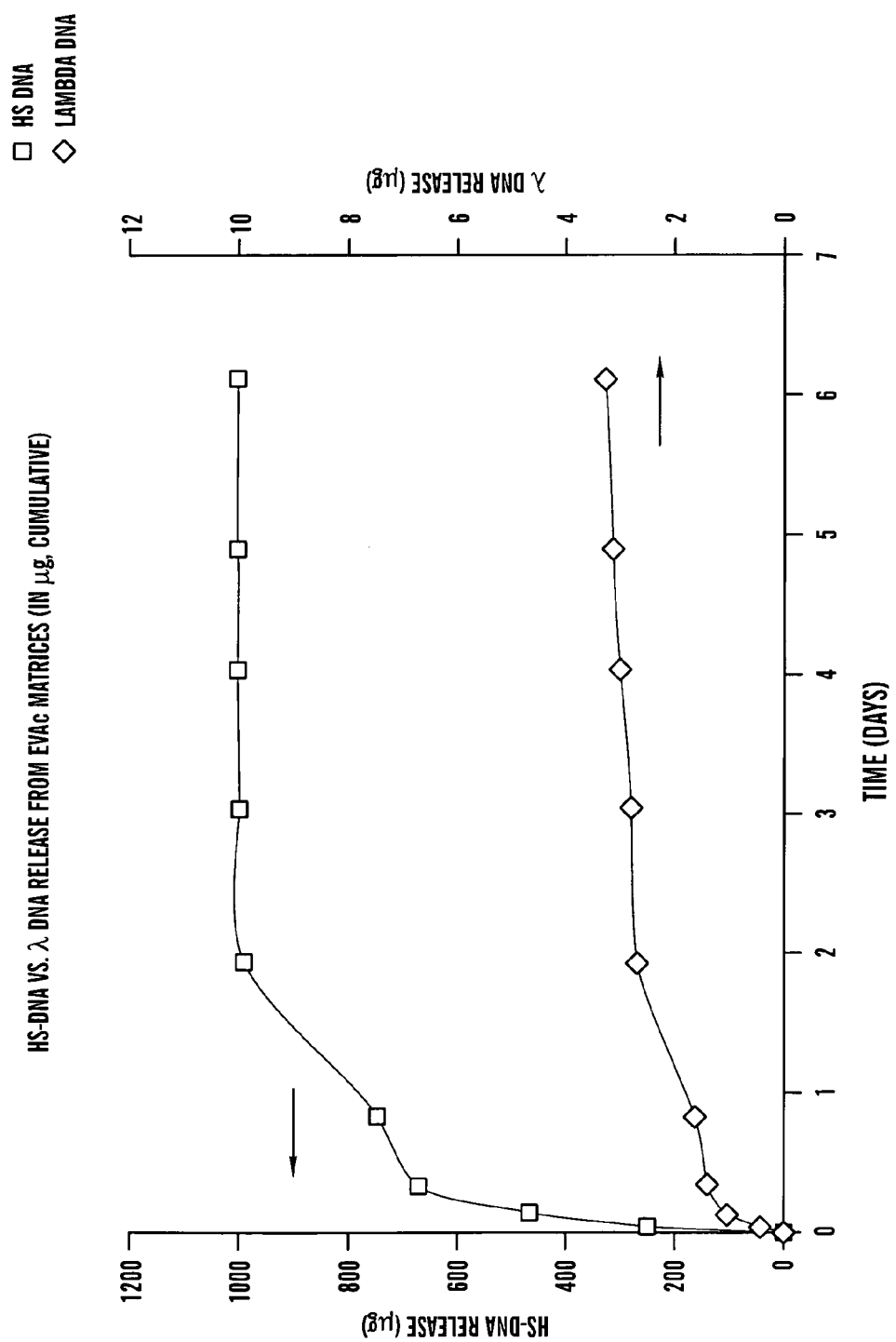
FIG. 2 is a graph depicting the release of herring sperm DNA ("HS-DNA") as compared to bacteriophage λ DNA ("λ DNA") from smaller EVAc matrices. Twenty mg of DNA (19.98 mg of HS-DNA (□) plus 0.02 mg of λ DNA (◇)) were encapsulated in EVAc matrices. Actual amounts of released λ DNA were determined by digitized agarose gel images. The secondary y-axis (right) is scaled to 1% of the primary y-axis (left) so that a graphical direct comparison between theoretical released λ DNA (which is 1% of total released DNA) and actual released λ DNA can be made.

To characterize the size dependency of DNA release from EVAc, 0.02 mg (1%) of λ DNA (48.5 kb) was co-dispersed with 1.98 mg of HS-DNA (0.1–0.6 kb) in an EVAc matrix (2 mg). One percent of total released DNA (determined by fluoroassays) was calculated as "theoretical released λ DNA". To determine the amount of actual λ DNA released, samples of released DNA were subjected to electrophoresis along with standard solutions containing an amount of λ DNA equal to 1% of DNA. The ratio of actual to theoretical λ DNA released was determined from these gels. On the average, large λ DNA molecules were released much slower than the smaller HS-DNA (FIG. 2), suggesting that DNA molecular weight is another important factor in determining the kinetics of encapsulated DNA release.

Figure 3:
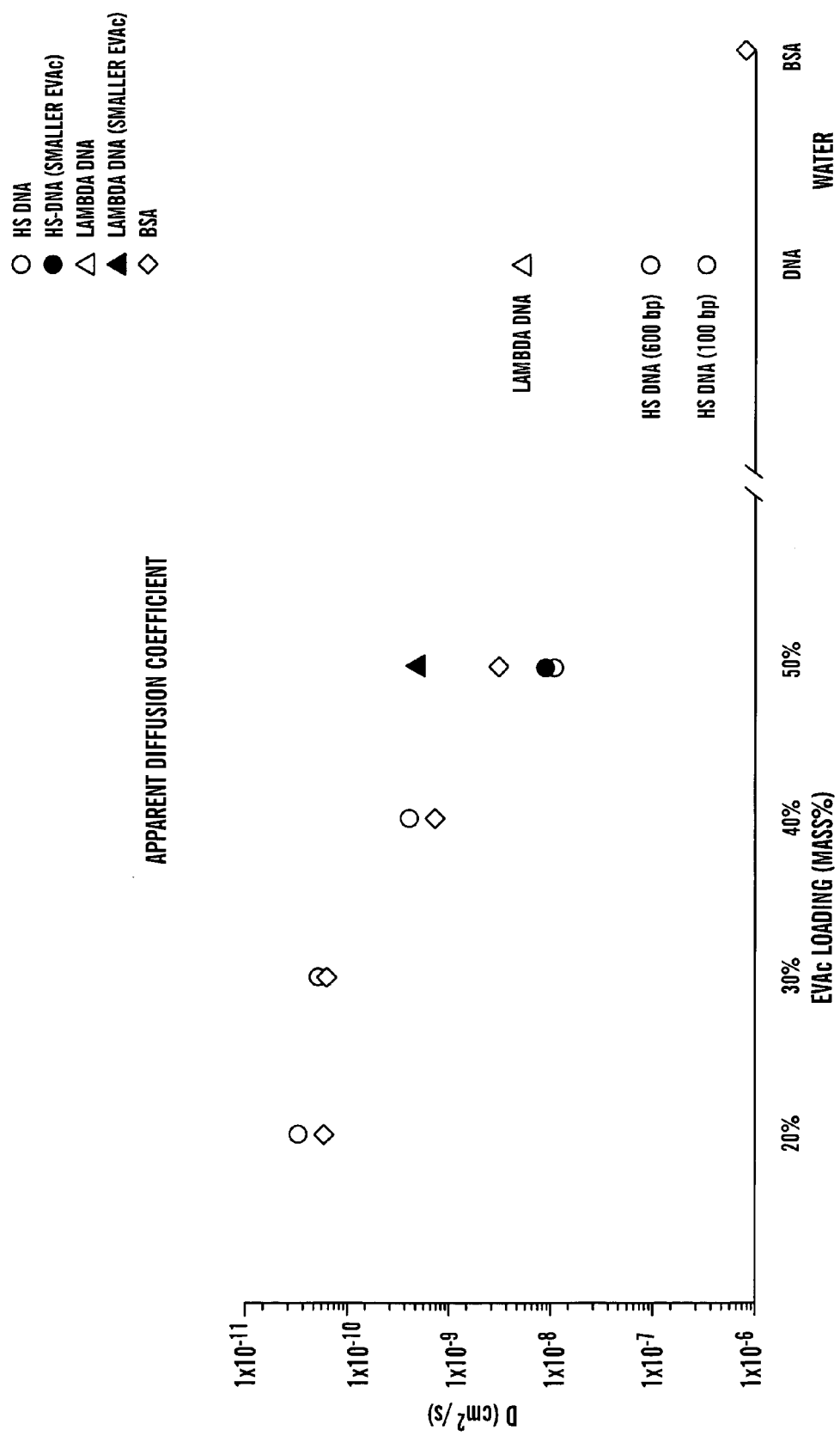
FIG. 3 is a scale illustrating the apparent diffusion coefficients ($D_{app}$) for HS-DNA, λ DNA, and bovine serum albumin ("BSA") from EVAc matrices. $D_{app}$ was calculated based on formula (1), infra. Previously published data (Soda et al., "Dynamic Light-Scattering Studies on Thermal Motions of Native DNAs In Solution," *Biophysical Chemistry* 20:185–200 (1984), which is hereby incorporated by reference) were used to establish a standard curve, and $D_{water, DNA}$ was obtained by interpolation. $D_{water, BSA}$ and $D_{app, BSA}$ were obtained from earlier studies (Saltzman et al., "Transport Rates of Proteins in Porous Materials with Known Microgeometry," *Biophys. J.* 55:163–171 (1989), which is hereby incorporated by reference). Symbols represent: ○, HS-DNA; HS-DNA from smaller EVAc matrices; Δ, λ DNA; ▲, λ DNA from smaller EVAc; and ◇, BSA.
Figure 4A:
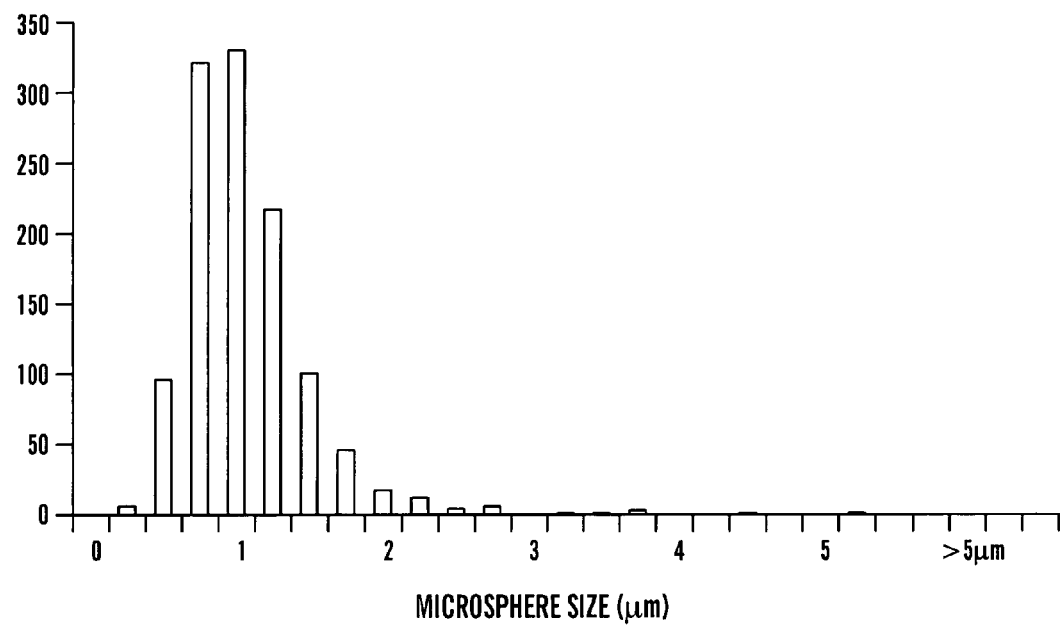
FIGS. 4A–F are graphs and images illustrating the size distribution and morphology of DNA encapsulated microspheres. All microsphere compositions were evaluated by scanning electron microscopy. Size distributions were based on more than 1000 particles visualized.
Figure 4B:
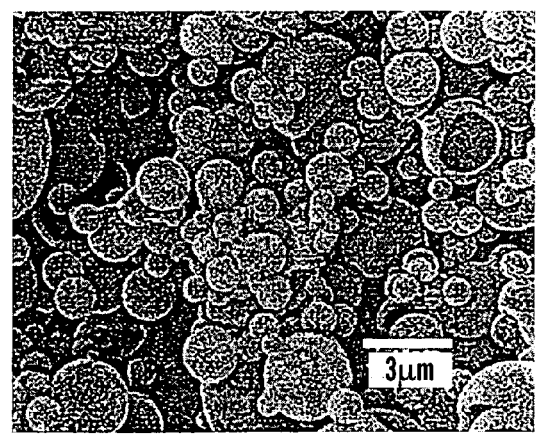
Figures 4C, 4D:
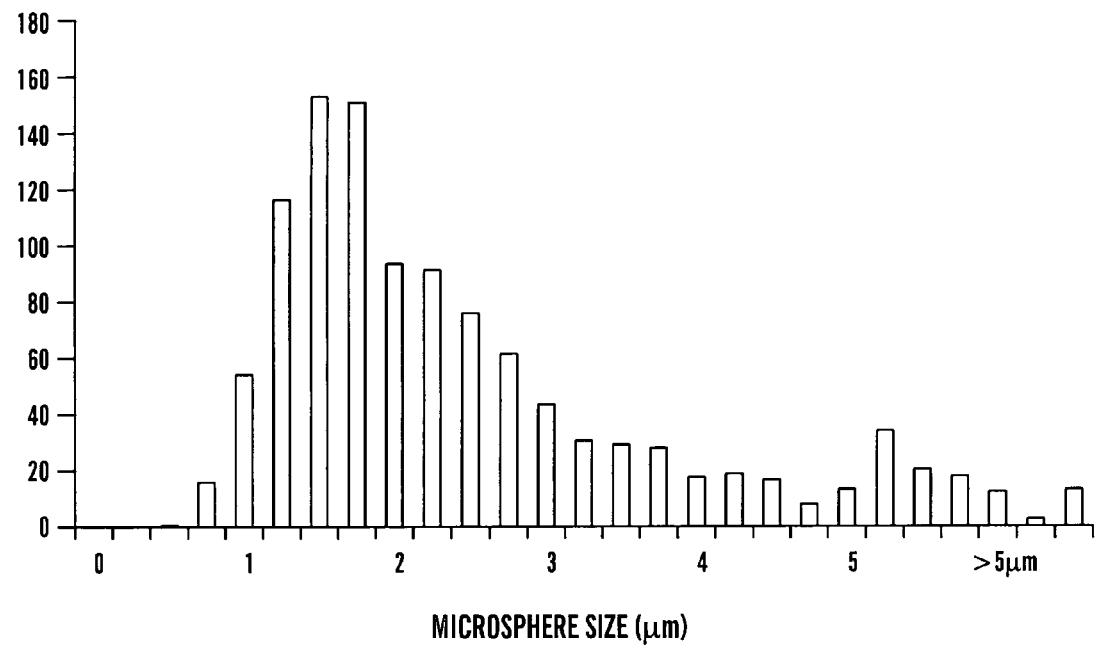
Figure 4E:
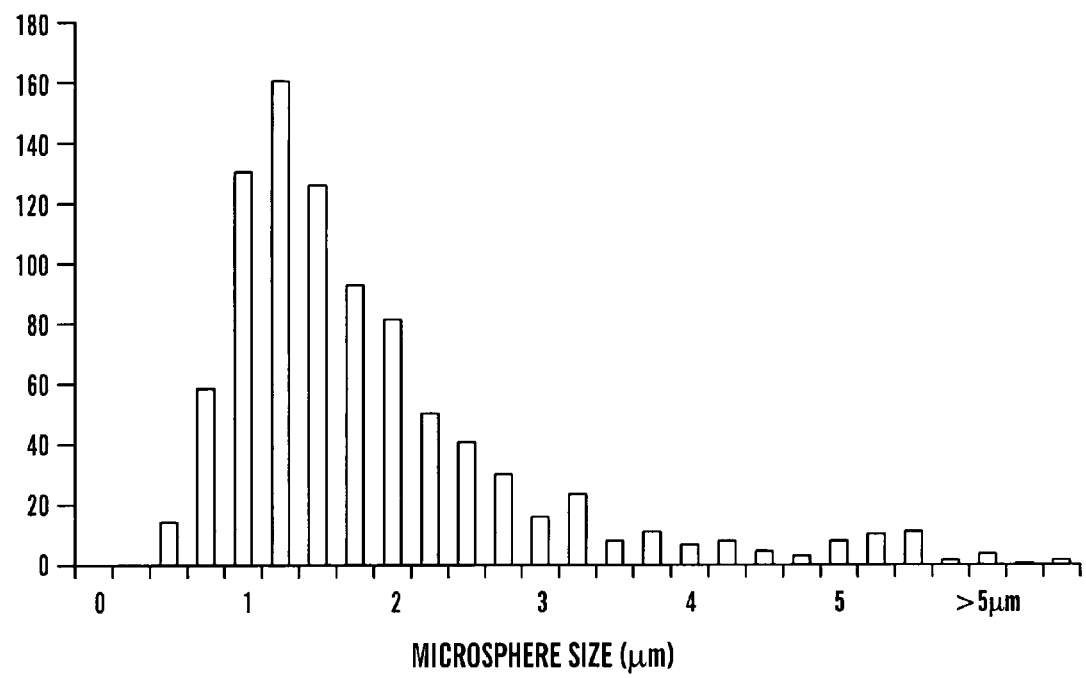
Figure 4F:
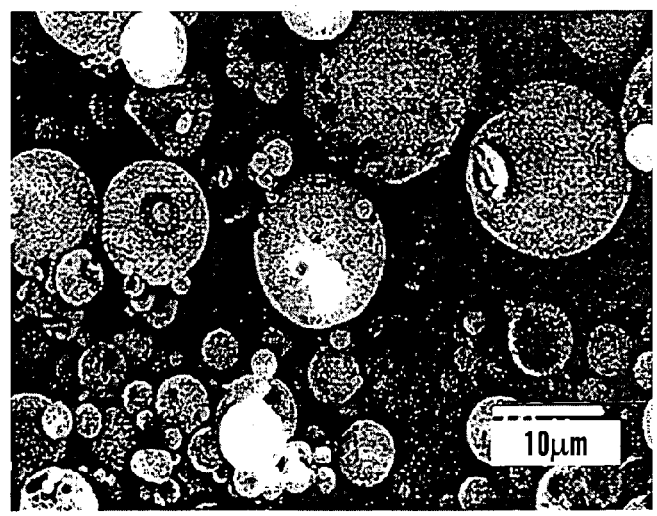

To quantify the difference in rate of release at early time, the apparent diffusion coefficient ($D_{app}$) for DNA release was determined by comparing data to a model for release from a disc (Saltzman et al., "Transport Rates of Proteins Materials with Known Microgeometry," *Biophys. J.* 55:163–171 (1989), which is hereby incorporated by reference):

$$\frac{M_1}{M_0} = \sqrt[4]{\frac{D_{app}t}{L^2\pi}} \quad \text{(Formula 1)}$$

where $M_t$ is the cumulative mass of DNA released, $M_0$ is the mass initially in the matrix, $D_{app}$ is the apparent diffusion coefficient, and L is the thickness of the disc. The apparent diffusion coefficients ($D_{app}$) for DNA from EVAc systems depend on both DNA molecular weight and loading. The $D_{app}$ of the smaller HS-DNA is about 22 times higher than that of the larger λ DNA. Among different DNA matrices, the $D_{app}$ of 50% loaded EVAc is about 28, 210, and 360 fold higher than that of 40%, 30%, and 20% loaded EVAc matrices, respectively (FIG. 3).

The release of proteins from EVAc matrices, first demonstrated over 20 years ago (Langer et al., "Polymers for the Sustained Release of Proteins and Other Macromolecules," *Nature* 263:797–800 (1976), which is hereby incorporated by reference), is controlled by diffusion. The time course of release can be modified by changing either the polymer or the encapsulants. For example, manipulation of the internal pore structure of a matrix (Saltzman et al., "Transport Rates of Proteins in Porous Materials with Known Microgeometry," *Biophys. J.* 55:163–171 (1989), which is hereby incorporated by reference), the molecular weight of the polymer within the matrix (Dang et al., "Dextran Retention in the Rat Brain Following Release From a Polymer Implant," *Biotechnol. Prog.* 8:527–532 (1992), which is hereby incorporated by reference), or addition of different co-dispersants (Krewson et al., "Stabilization of Nerve Growth Factor in Controlled Release Polymers and in Tissue," *J. Biomater. Sci. Polym. Ed.* 8:103–117 (1996), which is hereby incorporated by reference), can change the release profile significantly. A simple mathematical model can be employed to calculate the apparent diffusion coefficient, $D_{app}$, which can be used to compare quantitatively the release rates among different EVAc systems.

In this study, DNA was encapsulated in different amounts (20%, 30%, 40% and 50%) in DNA-EVAc systems with two different geometries (100 mg and 2 mg of EVAc). The controlled release of DNA was similar in all cases: an initial burst (phase I) was followed by a slow, but continuous, release (phase II). This trend was also seen in protein-EVAc controlled release systems, such as NGF-EVAc (Krewson et al., "Stabilization of Nerve Growth Factor in Controlled Release Polymers and in Tissue," *J. Biomater. Sci. Polym. Ed.* 8:103–117 (1996), which is hereby incorporated by reference). The release rate in the first phase of DNA release depended on loading. For example, the $D_{app}$ increased 13 fold from 20% to 40% loaded EVAc ($2.77 \times 10^{-11}$ vs. $3.55 \pm \times 10^{-10}$ cm$^2$/s). This was comparable to previously reported bovine serum albumin-EVAc (BSA-EVAc) systems, where the rate increased by 12 fold from 20% to 40% loading (Saltzman et al., "Transport Rates of Proteins in Porous Materials with Known Microgeometry," *Biophys. J.* 55:163–171 (1989), which is hereby incorporated by reference). Furthermore, the overall apparent diffusion coefficients within a specific loading were comparable between the HS-DNA-EVAc system and the BSA-EVAc system (FIG. 3). The similarity between DNA-EVAc and BSA-EVAc systems supports the notion that DNA release from EVAc polymers, like protein release, is controlled by diffusion.

Two different-sized DNA molecules were prepared (HS-DNA, average $M_w$=231 kDa, from 66 kDa to 396 kDa; and λ DNA, average $M_{w=32010}$ kDa) and their diffusion coefficients ($D_{app}$) were determined. (Since HS-DNA and λ DNA are loaded together, and both molecules are diffusing through exactly the same pore space, only the total loading matters.) The ratio of $D_{app, \lambda}$ to $D_{app, HS}$, which was about 22, was very close to the ratio of λ to HS DNA diffusion in water ($D_{water, \lambda}/D_{water, HS}$=19 to 67) (Soda et al., "Dynamic Light-Scattering Studies on Thermal Motions of Native DNAs In Solution," *Biophysical Chemistry* 20:185–200 (1984), which is hereby incorporated by reference), further evidencing that DNA release from EVAc systems is controlled by diffusion. This finding also suggests that the overall rate of gene release can be controlled by adjusting the size of the released DNA molecules.

A clinical situation may allow only certain sizes or geometries of delivery system. In addition, different molecular medicine procedures require different doses of DNA (e.g., gene therapy vs. DNA vaccination vs. antisense oligonucleotide therapy). Two different sizes of DNA-EVAc system: one large scale (100 mg of EVAc) and one small scale (2 mg of EVAc) were prepared. In both situations, the apparent diffusion coefficients were almost identical: $0.95 \times 10^{-8}$ cm$^2$/s vs. $1.01 \times 10^{-8}$ cm$^2$/s, confirming that the rate of release depends on the internal structure of the composite material, not overall geometry.

Example 2

Fabrication and Evaluation of DNA-Encapsulated Biodegradable Microspheres

The manufacturing procedures were a modification of the double emulsion (water/oil/water) solvent evaporation technique (Jones et al., "Poly(DL-lactide-co-glycolide)-encapsulated Plasmid DNA Elicits Systemic and Mucosal Antibody Responses to Encoded Protein After Oral Administration," *Vaccine* 15:814–817 (1997); Krewson et al., "Stabilization of Nerve Growth Factor in Controlled Release Polymers and in Tissue," *J. Biomater. Sci. Polym. Ed.* 8:103–117 (1996), which are hereby incorporated by reference). Briefly, 200 mg of PLGA ($M_n$=54,100, Birmingham Polymers, Birmingham, Ala.) or PLA ($M_n$=2000, and 300,000, Polysciences Inc. Warrington, Pa.) were dissolved in 2 ml of methylene chloride in a short glass test tube (5.8×1.4 cm). One mg of HS-DNA (10 mg/ml) was added drop-wise into the polymer solution while vortexing. Sonication was performed in crushed ice for 10 s (Tekmar Soni Disrupter model TM300, 40% duty cycle, microtip #4) to achieve a first emulsion, which appeared as a homogeneous milky mixture. Four ml of aqueous 1.0% PVA (poly (vinyl alcohol), 25000 $M_w$, 88 mol % hydrolyzed, Polysciences) was then slowly added to the milky first emulsion in ice. Sonication was repeated for another 10 s to form the second emulsion. Finally, the second emulsion was added to 100 ml of vigorously stirring 0.3% PVA solution, and the mixture was kept under continuous stirring at room temperature for 3 h to form microspheres. Centrifugation was performed at 3000 rpm at 4° C. for 10 min to collect microspheres. The collected microspheres were washed 3 times with milli-Q water before freezing in a −70° C. freezer. The microspheres were then lyophilized for 24 hours.

Biodegradable synthetic polymers were used to produce DNA-loaded microspheres. Most of the formulations tested resulted in particles greater than 100 μm in diameter with non-spherical morphology as shown in Table 2 below. By decreasing the amount of DNA, formulations based on PLA and PLGA produced the most consistent results. Despite the differences in polymer characteristics, the particles from each of these three formulations had similar size distributions and morphology (FIG. 4).

TABLE 2

Screening and characteristics of DNA microspheres

| Polymer | MW | Conc. (w/v %) | DNA (wt %) | Particle size (μm) | Morphology |
|---|---|---|---|---|---|
| PLA |  | 5% | 1% | >100 | Spherical |
|  |  | 10% | 0.5% | <10 or >100 | Spherical |
| PLA | 2K | 5% | 1% | 1.8 ± 1.4* | Spherical |
|  |  | 10% | 0.5% | <10 | Irregular |
|  |  | 15% | 0.25% | <5 | Spherical |
|  |  | 20% | 0.12% | <5 | Spherical |
| PLA | 50K | 5% | 1% | >100 | Spherical |
|  |  | 10% | 0.5% | >100 | Spherical |
| PLA | 100K | 5% | 1% | >100 | Spherical |
|  |  | 10% | 0.5% | <10 or >100 | Spherical |
| PLA | 300K | 5% | 1% | >100 | Spherical |
|  |  | 10% | 0.5% | 2.6 ± 2.1* | Spherical |
| PLGA (50:50) |  | 5% | 1% | <10 | Irregular |
|  |  | 10% | 0.5% | <10 | Irregular |
| PLGA (50:50) |  | 5% | 1% | >100 | Spherical |
|  |  | 10% | 0.5% | 0.95 ± 0.46* | Spherical |
| PLGA (75:25) |  | 5% | 1% | <10 | Irregular |
| PLCL (75:25) |  | 5% | 1% | <10 | Irregular |
|  |  | 10% | 0.5% | <10 | Irregular |

Concentration refers to w/v solution of polymers in 2.0 ml methylene chloride.
DNA (wt %) refers to theoretical DNA loading weight (DNA wt/Polymer wt).
Particle size and morphology was obtained by scanning electron microscopy.
*: these samples are used in controlled release study.

Figure 5A:
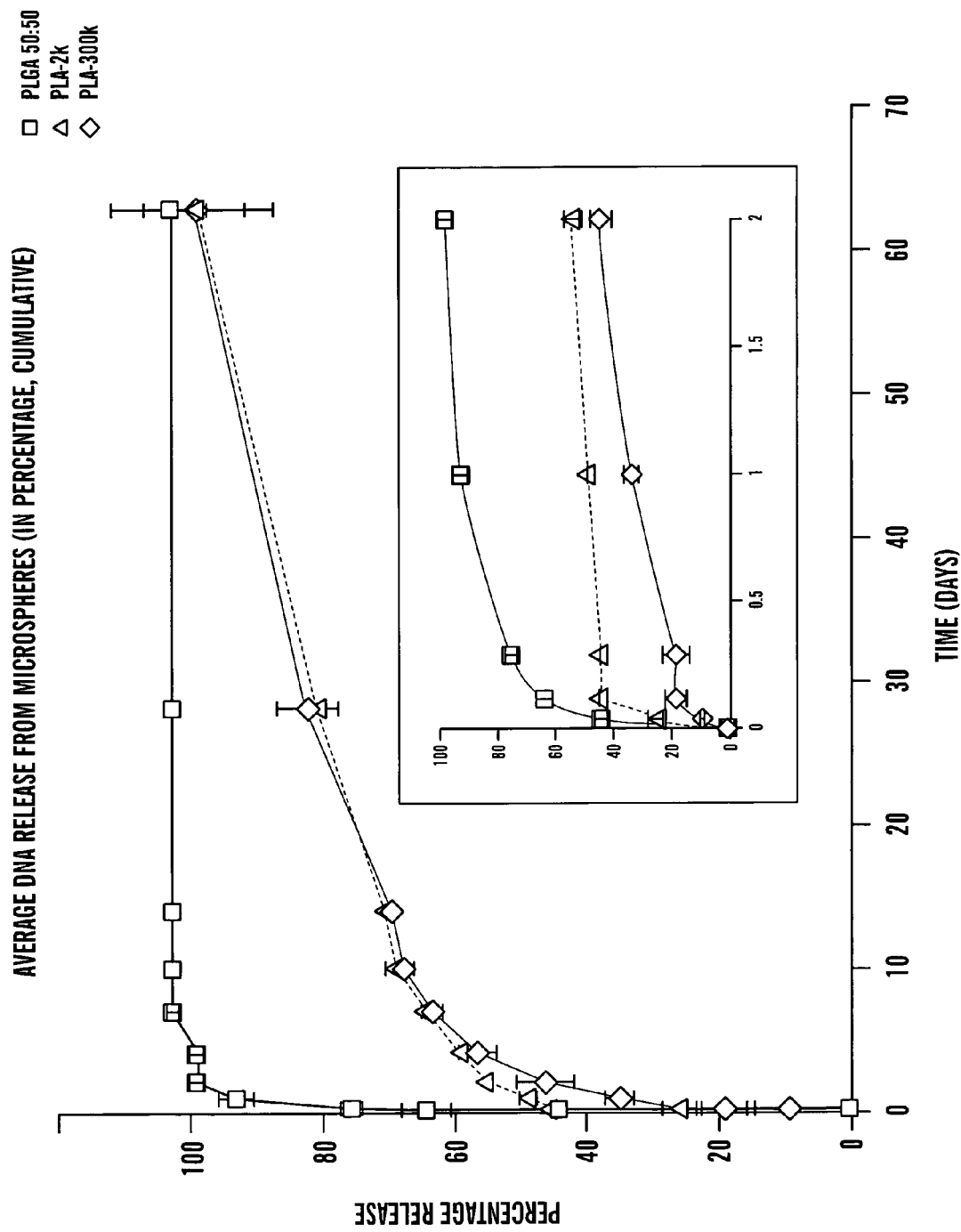
FIGS. 5A–B are graphs illustrating controlled DNA release from microspheres.

DNA release was similar among all three polymer systems: an initial burst of release was followed by a period of slow, but continuous, release (FIG. 5A). The cumulative percentage release differed for each formulation (FIG. 5A), despite the fact that these three polymers had similar sizes, size distributions, and surface morphology. Microspheres based on the lower molecular weight PLA-2k released >50% of their payload in the first few hours whereas PLA-300k released only 20% of its total DNA. In general, DNA encapsulated microspheres released most of their loaded DNA in about three weeks, somewhat faster than EVAc systems. PLGA microspheres showed faster DNA release than PLA 2k and PLA 300K; >90% of their DNA payload was released after only two days (FIG. 5A, inset).

Figure 5B:
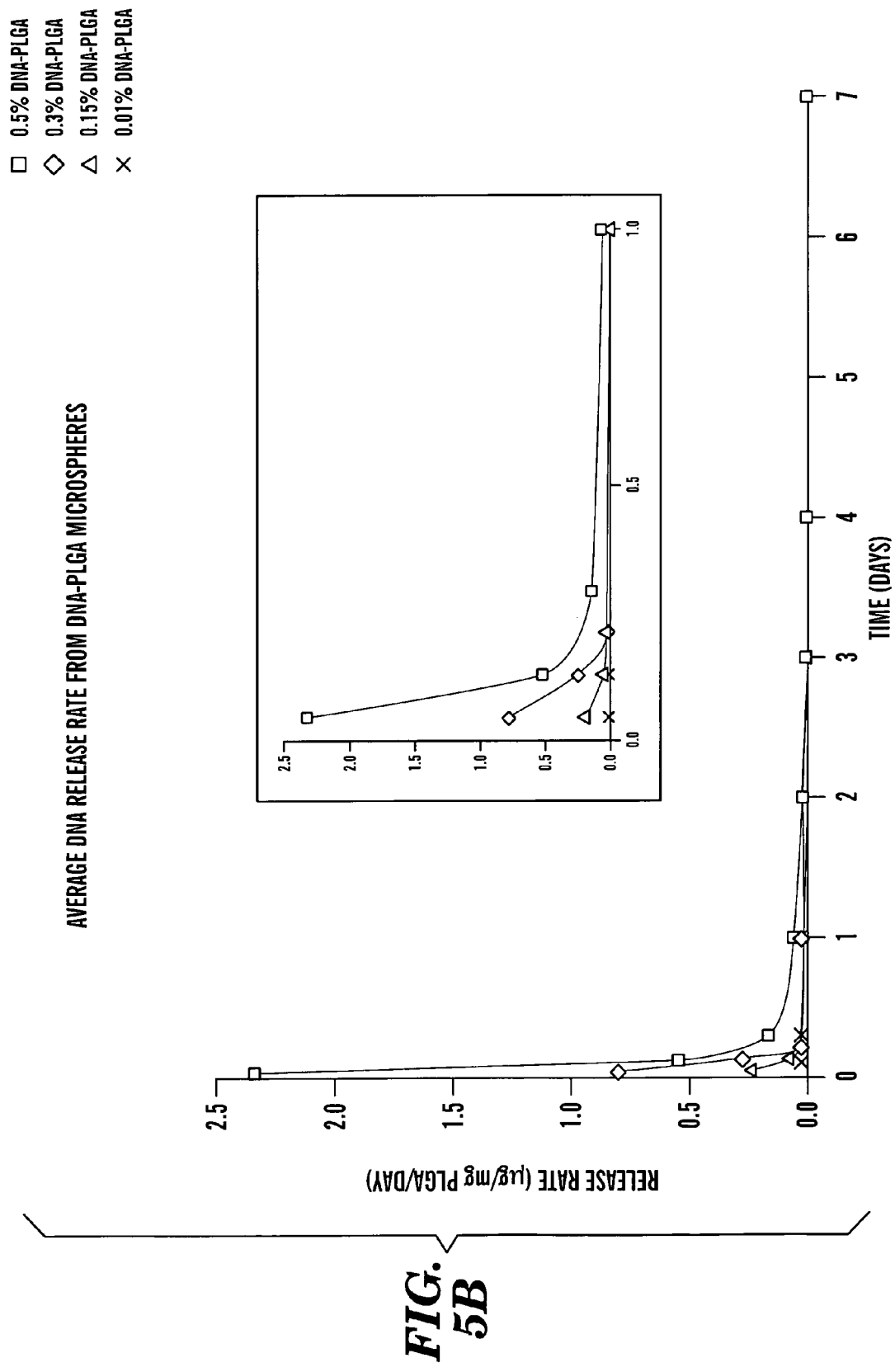

To investigate the effect of loading capacity on DNA delivery, PLGA microspheres loaded with different amounts of DNA (from 0.01% to 0.5%) were formulated (FIG. 5B). The time needed to release most of the encapsulated DNA depended on loading. Microspheres loaded with 0.5% DNA released 95% of its DNA after 48 hours incubation in PBS buffer, whereas microspheres loaded with 0.15% and 0.01% DNA released all DNA after only a few hours (FIG. 5B, inset).

Figure 6:
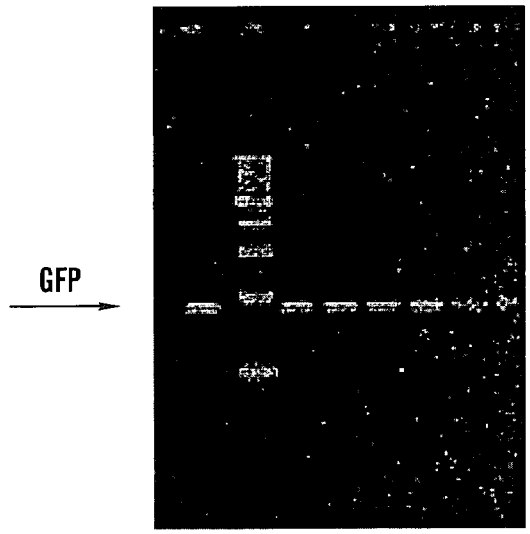
FIG. 6 is an image illustrating the integrity of released green fluorescent protein ("GFP") DNA from PLGA microspheres. PCR amplified GFP DNA was encapsulated in PLGA based microspheres and controlled release of GFP DNA was subject to 0.8% agarose gel electrophoresis. The gel is stained with SYBR II fluorescence dye. Lane 1: 0.5 μg of GFP DNA without encapsulation (input DNA, controls); lane 2: molecular weight marker (1 kb ladder); lanes 3 and 4 (duplicates): 0.5 μg of released DNA after 2 hour incubation; lanes 5 and 6: 0.5 μg of released DNA after 24 hour incubation; and lanes 7 and 8: 0.5 μg of released DNA after 168 hours (1 week) of incubation.

Green fluorescence protein gene (GFP), amplified by PCR, was used to examine the integrity and functionality of DNA released from biodegradable DNA delivery systems. Agarose gel electrophoresis indicated no detectable DNA degradation among released DNA after 1 d, and only 20% degradation was detected after 7d (FIG. 6). Expression of GFP genes within CHO cells was followed by fluorescence microscopy. No significant differences were observed between non-encapsulated GFP DNA and released GFP DNA, indicating that the released GFP DNA is capable of expression.

On the other hand, release of DNA from a microsphere delivery system depends on both erosion (subsequent to hydrolysis) and diffusion. A variety of factors can influence DNA release from microspheres, including chemical properties of the polymer, molecular weight, particle size and morphology, DNA loading, and DNA solubility. While this finding suggests many approaches for controlling DNA release from microspheres, no simple mathematical model can be applied to predict or quantify release rates in these systems.

The release profiles of PLA based DNA-microsphere systems exhibited a similar bi-phasic trend: an initial burst followed by a slow release. The microspheres based on the lower molecular weight PLA-2k, however, released a greater amount of loaded DNA than microspheres based on the high molecular weight PLA-300k. This can be attributed to the fact PLA-2k possesses a higher rate of degradation since the polyesters have elevated amounts of end-carboxylic groups. Among all 3 DNA-microsphere delivery systems, the fastest release of DNA was from PLGA based microsphere: 95% of their DNA load was released after only two days. Since copolymers of poly (D, L-lactide) and polyglycolide usually have lower glass transition temperatures ($T_g$) and lower crystallinity ($T_m$), PLGA shows a greater susceptibility to hydration than PLA. Therefore, it is expected that PLGA releases DNA at a much faster rate than PLA.

Example 3

Incorporation of DNA and Co-Dispersants into EVAc Matrices

One hundred mg of the co-dispersants Dextran 500, Dextran-DEAE 500, Dextran sulfate 500, Ficoll 400, Ficoll 70, and OVA were individually dissolved in milli-Q water. The resulting solution was mixed with the HS-DNA solution (10 mg/ml) at a DNA:co-dispersant mass ratio of 1:60 and then the mixture was lyophilized overnight. The resulting dry powder was reduced to a size of less than 178 µm before incorporation into EVAc matrices.

Incorporation of the mixture containing the HS-DNA and co-dispersant was performed according to the procedures set forth in Example 1. The resulting EVAc slabs were corked into three disks sized 1 mm in thickness and 2 mm in diameter, having an approximate mass of 8–10 mg.

Figure 7:
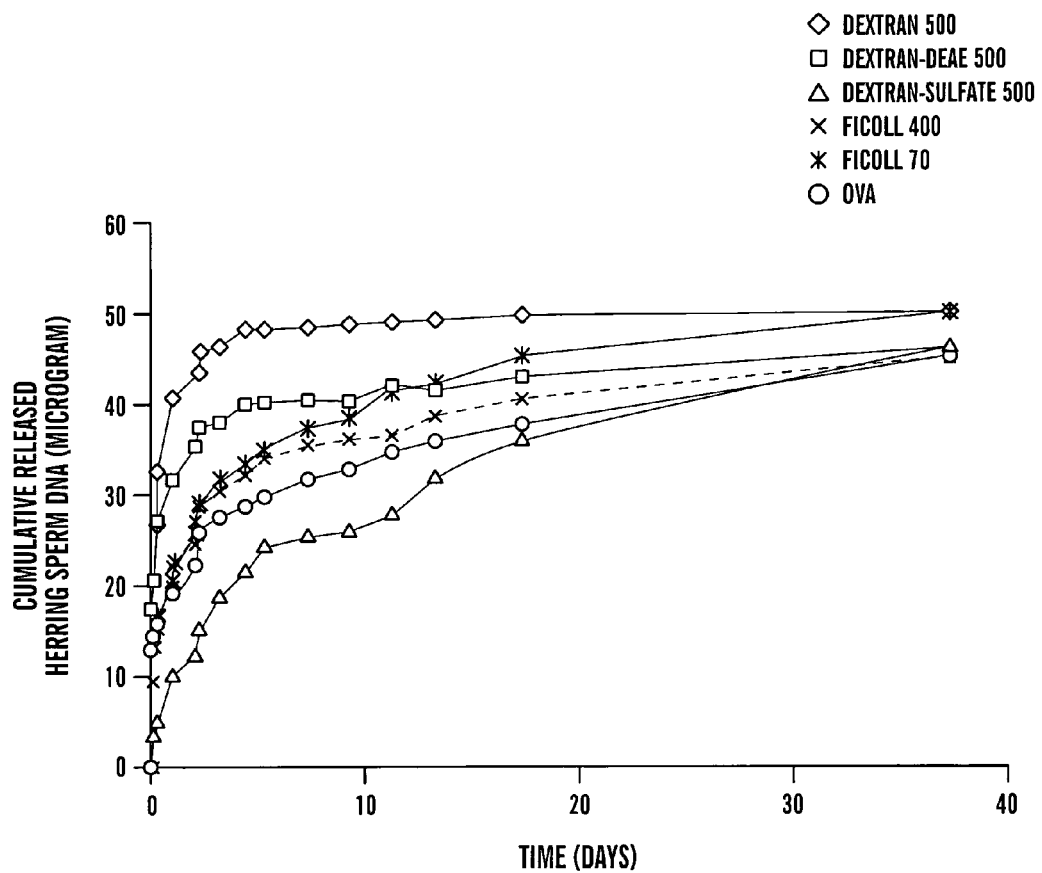
FIG. 7 is a graph illustrating the controlled HS-DNA release from EVAc matrices with different co-dispersants. Each data point is the average of triplicate EVAc discs. The loading for all the EVAc discs is 50%. The ratio of HS-DNA to the co-dispersants is 1:60. Different co-dispersants are reflected by each of the symbols according to the legend.

As shown in FIG. 7, the release of HS-DNA from the EVAc disks into buffered solution was measured as described in Example 1. Although all of the co-dispersants slowed the release of HS-DNA from the EVAc matrix, Dextran-sulfate 500 produced the most consistent release over the course of time.

Example 4

Transfection of CHO Cells with Plasmid Including β-Galactosidase Gene in EVAc Matrix with Various Uptake Agents A plasmid including a β-galactosidase gene, pVAX1/LacZ, was purchased from Invitrogen Corp. Plasmid pVAX1/LacZ was amplified in *Escherichia coli* and purified by Wizard® PureFection Plasmid DNA Purification System (Promega, Madison, Wis.). The purified plasmid DNA was re-dissolved in nuclease-free water and stored at −20° C. for later use.

EVAc matrixes were prepared substantially as described in Example 1. Briefly, 100 mg of Ficoll 400 (Sigma, St. Louis, Mo.) was dissolved in milli-Q water to form a first solution. A second solution was prepared using 10 µg of the plasmid pVAX1/LacZ (184 µg/ml), which was mixed with different transfection reagents according to the manufacturer's instructions (TRANSFAST™ Transfection Reagent was purchased from Promega Corp; SUPERFECT™ Transfection Reagent and EFFECTENE™ were purchased from Qiagen Inc.). The two solutions were then combined and lyophilized overnight. The resulting dry powder was reduced to a size of less than 178 µm before incorporation into EVAc matrices.

Incorporation of the mixture containing the plasmid DNA and cellular uptake agent was performed according to the procedures set forth in Example 1. The resulting EVAc-slabs were stored at −20° C. for later use.

On the day before transfection, $3.6 \times 10^5$ CHO cells per well were plated in a 6-well tissue culture plate. After 24 h incubation in the incubator (37° C., 5% $CO_2$), cells were washed once with filtered PBS, 4 ml of the growth medium (F-12K Nutrient Mixture (Kaighn's modification) containing 10% Fetal Bovine Serum and 1% Penicillin-Streptomycin, Life Technologies) was added into each well. The formulated EVAc discs were gently placed into each well. The plate was carefully returned to the incubator for 48 h before analysis. After 48 h incubation, medium and EVAc discs were carefully removed from each well and cells were washed once with PBS. PBS was removed and 1.5 ml per well of the fixative (2% formaldehyde, 0.2% glutaraldehyde in PBS) was added. The plate was incubated at room temperature for 20 min. Then, the fixative was removed and cells were washed three times with PBS. Cells with 1 ml per well of the staining solution (1 part of X-gal solution with 19 parts of Iron buffer, Boehringer Mannheim GmbH, Germany) were incubated for 3 hour at 37° C. The staining solution was removed and cells were washed again with PBS. Fresh PBS was added after the last wash. Stained cells (transfected cells) were counted under light microscope without phase contrast.

Figure 8:
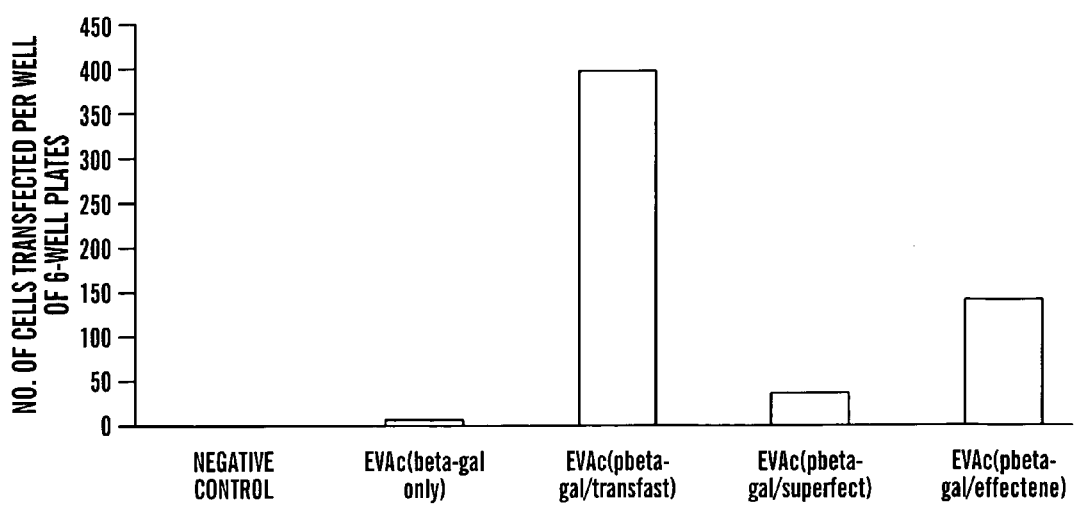
FIG. 8 is a graph illustrating the results for in vitro transfection of COS cells using EVAc discs containing plasmid DNA encoding β-galactosidase along with different transfection reagents. In the lables on the X-axis, "pbeta-gal" refers to the plasmid encoding β-galactosidase.

As shown in FIG. 8, the EVAc discs containing no DNA (negative control), plasmid DNA (control), and the plasmid DNA with various cellular uptake agents displayed markedly different transfection rates in CHO cells. Of the cellular uptake agents included in the EVAc matrices, TRANSFAST™ afforded the highest transfection rates, although each of them resulted in enhanced uptake of the plasmid.

Example 5

Preparation of PLGA Microspheres Containing Plasmid Including Nucleotide Sequence Coding for Sperm-Specific Lactate Dehydrogenase-C4

The plasmid pcDNA3-LDH-C4 contains a sequence coding for sperm-specific lactate dehydrogenase-C4 ("LDH-C4"). LDH-C4 is a homotetramer of the C subunit of lactate dehydrogenase; purified mouse LDH-C4 has been shown to reduce fertility in female mice. The plasmid pcDNA3-LDH-C4 was obtained from Professor Erwin Goldberg (Department of Biochemistry, Molecular Biology and Cell Biology at Northwestern University). pcDNA3-LDH-C4 was amplified in the *Escherichia coli* and purified by Wizard® PureFection Plasmid DNA Purification System (Promega, Madison, Wis.). The purified DNA was re-dissolved in nuclease-free water and then stored at −20° C. for later use.

400 mg of PLGA (50:50, $M_n$=54, 100, Birmingham polymers, Birmingham, Ala.) was dissolved in 2 ml of methylene chloride in a glass test tube. 200 µl of the aqueous solution containing 50 mg/ml Ficoll 400 and either 0.5 mg/ml (Formulation 1) or 0.17 mg/ml (Formulation 2) pcDNA3-LDH-C4 was added drop-wise into the polymer solution while vortexing. Sonication was performed in crushed ice for 10 s (Tekmar Soni Disrupter model TM300, 40% duty cycle, microtip #4) to achieve a first emulsion, which appeared as a homogeneous milky mixture. Five ml of aqueous 1.0% PVA (poly (vinyl alcohol), 25000 $M_w$, 88 mol % hydrolyzed, Polysciences) was then slowly added to the milky first emulsion in ice. Sonication was repeated for another 10 s to form the second emulsion. Finally, the second emulsion was added to 100 ml of 0.3% PVA solution while vigorously stirring, and the mixture was kept under continuous stirring at room temperature for 3 h to form microspheres. Centrifugation was performed at 3000 rpm at 4° C. for 10 min to collect microspheres. The collected microspheres were washed 3 times with milli-Q water before freezing in the −70° C. freezer. The microspheres were then lyophilized for 24 hours.

The loading efficiency for the microspheres of Formulation 1 and Formulation 2 were calculated, as a percentage, by dividing the weight of DNA used for preparing a given weight of microsphere by the weight of DNA encapsulated in a given weight of microsphere. The loading efficiency of Formulation 1 microspheres was about 10.7% and the loading efficiency of Formulation 2 microspheres was about 3.6%

Figure 9:
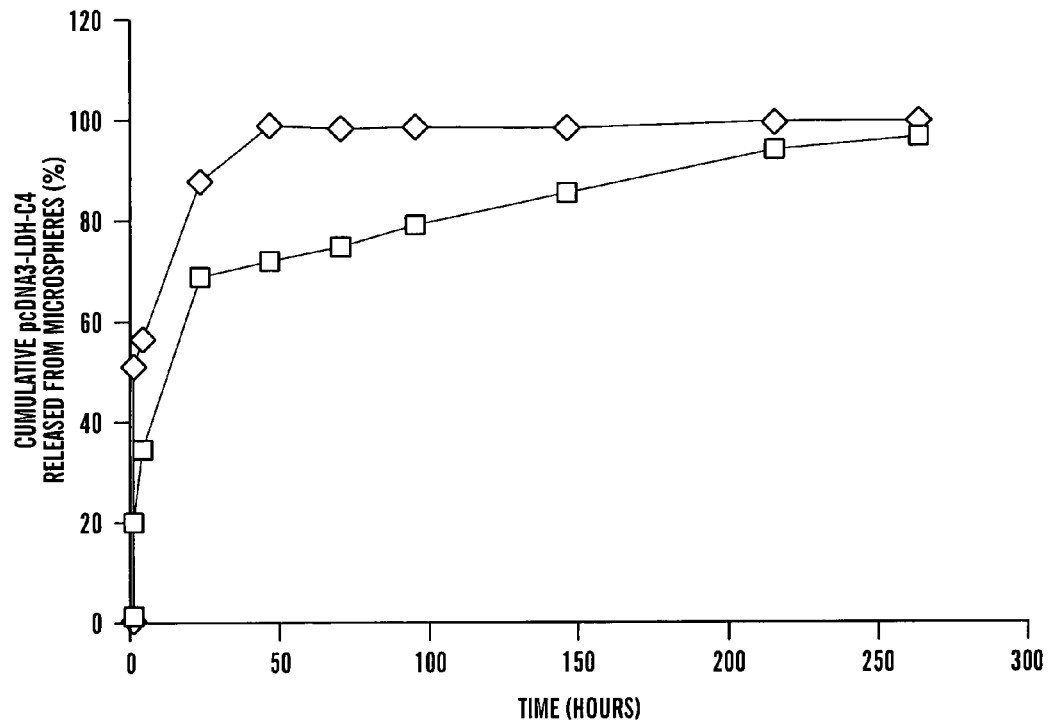
FIG. 9 is a graph illustrating the controlled release profile of plasmid DNA from PLGA (50:50) microspheres differing in ratio of DNA to Ficoll 400, 1:100 (◇) and 1:300 (□). DNA-encapsulated microspheres were incubated in PBS (pH=7.4) at 37° C. with shaking. The DNA released in supernatants at different time points was quantified by PicoGreen method, infra.

As shown in FIG. 9, the effects of different ratios of Ficoll 400 co-dispersant on plasmid release are shown (DNA: Ficoll of 1:100 (◇) and 1:300 (□)). Specifically, 40 mg of microspheres were incubated in 1 ml of PBS containing 0.02% gentamicin sulfate for up to 12 days at 37° C. with gentle shaking. Periodically, 0.5 ml of buffer was collected after centrifugation and replaced with 0.5 ml of fresh buffer. The collected samples were assayed by PicoGreen method (discussed supra). The percentage of DNA released from the microspheres at each time point was obtained by using the cumulative amount of DNA released from 400 mg microspheres at each time point to time 100 and then dividing the result by the total DNA encapsulated in the 40 mg of microspheres. As shown by the cumulative release graphs, the higher loading of the Ficoll 400 contributed to a slower release of the plasmid DNA.

Example 6

DNA Vaccination of Mice with Microspheres Containing Plasmid Including Nucleotide Sequence Coding for Sperm-Specific Lactate Dehydrogenase-C4

The microspheres produced in Example 5 were used in a DNA vaccination experiment.

Eight to nine week Balb/c female mice (Harlan, Frederick, Md., USA) were immunized by orally feeding pcDNA3-LDH-C4 in PBS (Group 1), pcDNA3-LDH-C4 encapsulated in microspheres which were suspended in PBS (Group 2), or PBS via a feeding needle (Group 3). In Group 1, each of 4 Balb/c female mice was immunized by 60 µg DNA in 500 µl PBS containing 50 mg/ml Ficoll 400. In Group 2, each of 4 Balb/c female mice was immunized by 30 µg DNA encapsulated in microspheres (using a mixture of 50 mg Formulation 1 microspheres and 30 mg Formulation 2 microspheres) suspended in PBS. In Group 3, each of 3 Balb/c female mice was immunized by 500 µl PBS. Group 3 was used as negative control.

Vaginal washes were collected weekly, including one week before immunization and one week after immunization. The animals were anethetized with methoxyflurane (Metofane). Vaginal washes were collected by introducing 20 µl PBS into vagina and pipetting in and out 10 times. This procedure was repeated 3 times for a total of 60 µl. Vaginal washes were centrifuged at 10,000 rpm for 10 minutes at room temperature, and the supernatants were transferred into 1 ml centrifuge tubes and stored frozen (−20° C.) until analysis.

A 96-well Immunosorbant plate (Dynatech Immunon IV, Dynex, Chantilly, Va.) was coated 3 hours at room temperature with 5 µg per ml of LDH-C4 antigen in carbonate coating buffer (pH=9.6). A wash solution of PBS containing 0.05% Tween 20 was used to rinse the plate three times. Then, any non-specific adsorption sites were blocked with SuperBlock® Blocking Buffer in PBS (Pierce, Rockford, Ill.). After one-half hour of incubation at room temperture with shaking, samples were diluted 1:50 in PBS (pH=7.4, containg 0.05% BSA), and 100 µl of the solution was added to each well. The plate was covered with parafilm and incubated overnigh at 4° C. After another wash, the plate was incubated for 1 h with horseradish peroxidase (HRP)-conjugated goat anti-mouse IgA (Zymed, South San Francisco, Calif.) diluted 1:200 with PBS containing 0.05% BSA and 0.05 Tween20. The plate was washed again. The alkaline phosphate was developed with p-nitrophenyl phosphate (Sigma, St. Louis, Mo.) for 5 min at room temperture with shaking and for 25 min at 37° C. in a darken room. The reaction was stopped by addition of 50 µl 3M NaoH per well. The optical density (OD) was read at 405 nm on a THERMOmax microplate reader and a Macintosh computer (SOFTMAX, version 2.01).

Figure 10:
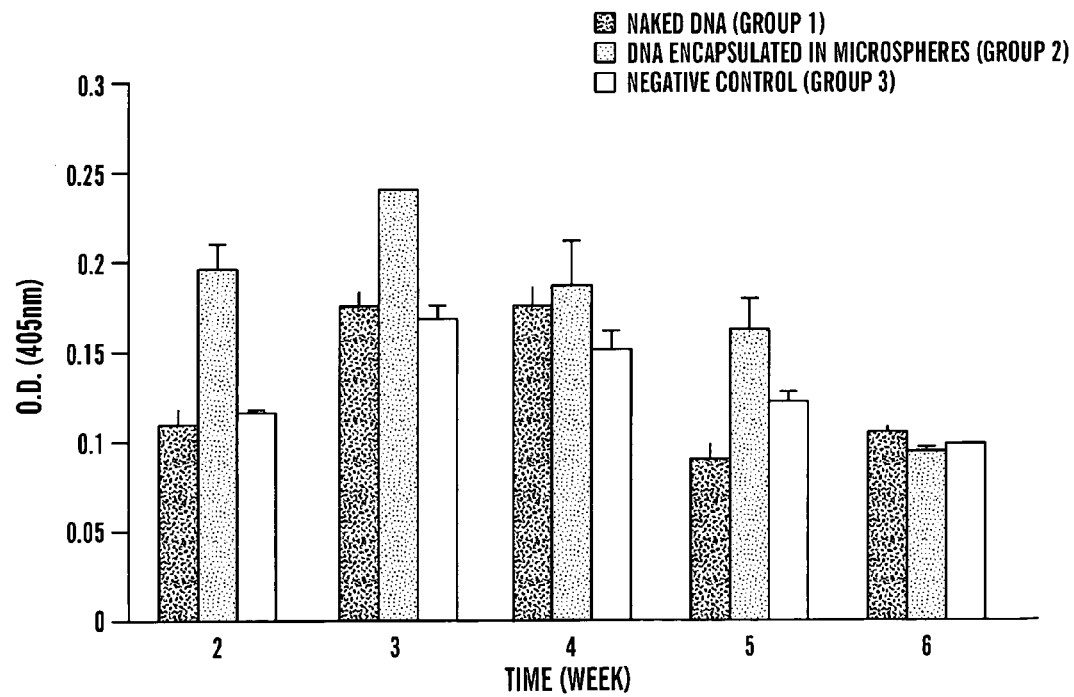
FIG. 10 is a graph illustrating the recognition of IgA antibody specific to LDH-C4 peptide in vaginal washes of Balb/c mice immunized by PLGA (50:50) microspheres containing plasmid DNA (coding for LDH-C4) or naked plasmid DNA. Error bars in the graphs show the variation of assay by ELISA for the same sample. All the data shown are

Analysis of the results shown in FIG. 10 indicates that immunization was enhanced by encapsulation of the plasmid in the polymeric microspheres.

By way of comparison, intravaginal implantation of an EVAc polymeric matrix containing pcDNA3-LDHC4 and TRANSFAST™ also produced similar immunization results. It was also observed that the DNA-liposome complex released from polymer matrices in a controlled, sustained fashion and showed much higher transfection efficiency than naked plasmid DNA, along with much lower cytotoxicity than the same dose of DNA-liposome complex administrated all at once.

Although the invention has been described in detail for the purposes of illustration, it is understood that such detail is solely for that purpose, and variations can be made therein by those skilled in the art without departing from the spirit and scope of the invention which is defined by the following claims.

SEQUENCE LISTING

```
<160> NUMBER OF SEQ ID NOS:  21

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 1

Pro Lys Lys Arg Lys Val Glu
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 2
```

-continued

Pro Pro Lys Lys Ala Arg Glu Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: nuclear
      translocation signal

<400> SEQUENCE: 3

Pro Ala Ala Lys Arg Val Lys Leu Asp
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: nuclear
      translocation signal

<400> SEQUENCE: 4

Lys Arg Pro Arg Pro
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: nuclear
      translocation signal

<400> SEQUENCE: 5

Lys Ile Pro Ile Lys
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: nuclear
      translocation signal

<400> SEQUENCE: 6

Gly Lys Arg Lys Arg Lys Ser
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: nuclear
      translocation signal

<400> SEQUENCE: 7

Ser Lys Arg Val Ala Lys Arg Lys Leu
 1               5

<210> SEQ ID NO 8
<211> LENGTH: 9
<212> TYPE: PRT
<213> ORGANISM: Artificial Sequence

```
<220> FEATURE:
<223> OTHER INFORMATION: Description of Artificial Sequence:  nuclear
      translocation signal

<400> SEQUENCE: 8

Ser His Trp Lys Gln Lys Arg Lys Phe
  1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 9

Pro Leu Leu Lys Lys Ile Lys Gln
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 10

Pro Gln Pro Lys Lys Lys Pro
  1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 11

Gly Lys Arg Lys Lys Glu Met Thr Lys Gln Lys Glu Val Pro
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 12

Gly Arg Lys Lys Arg Arg Gln Arg Arg Arg Ala Pro
  1               5                  10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 13

Asn Tyr Lys Lys Pro Lys Leu
  1               5
```

-continued

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 14

His Phe Lys Asp Pro Lys Arg
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 15

Ala Pro Arg Arg Arg Lys Leu
  1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 16

Ile Lys Arg Leu Arg Arg
  1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 17

Gly Arg Arg
  1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:  nuclear
      translocation signal

<400> SEQUENCE: 18

Ile Lys Arg Gln Arg Arg
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:  nuclear
      translocation signal
```

```
<400> SEQUENCE: 19

Ile Arg Val Arg Arg
 1               5

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 20
ctgattctgt ggataaccgt att                                          23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 21
tggaacaaca ctcaaccota tct                                          23
```

The invention claimed is:

1. A nucleic acid delivery system comprising:
a polymeric structure formed of a biocompatible polymer and
a mixture comprising one or more nucleic acid molecules and a first co-dispersant, which is an inert polymer that is different from the biocompatible polymer and does not interact with the one or more nucleic acid molecules, the mixture being contained within the polymeric structure, wherein the first co-dispersant is present in an amount effective to reduce the rate of diffusion of the one or more nucleic acid molecules from the polymeric structure for sustained release of the one or more nucleic acid molecules as compared to a polymeric structure comprising the one or more nucleic acid molecules absent an effective amount of the first co-dispersant.

2. The nucleic acid delivery system according to claim 1, wherein the polymeric structure is a matrix or a microsphere.

3. The nucleic acid delivery system according to claim 2, wherein the polymeric structure is a matrix which is less than about 10 cm in length.

4. The nucleic acid delivery system according to claim 2, wherein the polymeric structure is a microsphere which is less than about 10 μm in length.

5. The nucleic acid delivery system according to claim 1, wherein the biocompatible polymer is poly(ethylene-co-vinyl acetate), poly(lactide-co-glycolide), poly(caprolactone), poly(lactide), polyglycolide, polyanhydride, polyorthoester, polyphosphazene, proteinaceous polymer, polyester, silicone, or combinations thereof.

6. The nucleic acid delivery system according to claim 1, wherein the one or more nucleic acid molecules are the same or different with each being inserted in a heterologous expression vector.

7. The nucleic acid delivery system according to claim 6, wherein the nucleic acid molecule is inserted in the expression vector in sense orientation.

8. The nucleic acid delivery system according to claim 7, wherein the nucleic acid molecule is a DNA molecule which encodes a translatable RNA transcript encoding a protein or polypeptide.

9. The nucleic acid delivery system according to claim 7, wherein the nucleic acid molecule is a DNA molecule which encodes an untranslatable RNA transcript.

10. The nucleic acid delivery system according to claim 7, wherein the nucleic acid molecule is an RNA molecule.

11. The nucleic acid delivery system according to claim 6, wherein the nucleic acid molecule is inserted in the expression vector in antisense orientation.

12. The nucleic acid delivery system according to claim 11, wherein the nucleic acid molecule is a DNA molecule.

13. The nucleic acid delivery system according to claim 11, wherein the nucleic acid molecule is an RNA molecule.

14. The nucleic acid delivery system according to claim 1, wherein the inert polymer is selected from the group consisting of herring sperm DNA, a random or non-coding DNA having a molecular weight of about 100 kDa to about 2000 kDa, a DNase-free filler, a DNase-free bulk protein, DNase free peptide, glycoproteins, peptide-nucleic acids, and combinations thereof.

15. The nucleic acid delivery system according to claim 1, wherein each of the one or more nucleic acid molecules is a DNA molecule, the nucleic acid delivery system further comprising:

a nucleus translocation polypeptide coupled individually to each DNA molecule.

16. The nucleic acid delivery system according to claim 1, wherein the mixture further comprises a cellular uptake agent.

17. The nucleic acid delivery system according to claim 16, wherein the cellular uptake agent is a target cell receptor binding ligand.

18. The nucleic acid delivery system according to claim 16, wherein the cellular uptake agent is coupled individually to each of the one or more nucleic acid molecules.

19. The nucleic acid delivery system according to claim 1, wherein the mixture further comprises a second co-dispersant which stabilizes the one or more nucleic acid molecules.

20. The nucleic acid delivery system according to claim 19, wherein the second co-dispersant is selected from the group consisting of a cationic polymer, a DNA binding protein, and a DNase inhibitor.

21. The nucleic acid delivery system according to claim 20, wherein the second co-dispersant is a cationic polymer selected from the group consisting of poly-L-lysine, poly-L-lysine conjugates and copolymers, polyethyleneimine, diethylaminoethyl-dextran, cationic dendritic polymers, and combinations thereof.

22. The nucleic acid delivery system according to claim 20, wherein the second co-dispersant is a DNA binding protein selected from the group consisting of histones, histone-1 derived peptide, cationic polypeptides, protamines, spermine, spermidines, and combinations thereof.

23. The nucleic acid delivery system according to claim 20, wherein the second co-dispersant is a DNase inhibitor is DMI-2.

24. A composition comprising:
a nucleic acid delivery system according to claim 1 and
a pharmaceutically-acceptable carrier.

25. A method of delivering a nucleic acid molecule into a cell in a patient comprising:
providing a nucleic acid delivery system according to claim 1 and
administering the nucleic acid delivery system to the patient under conditions effective to contact a cell in the patient with the one or more nucleic acid molecules following release from the nucleic acid delivery system, wherein the one or more nucleic acid molecules are taken up by the cell.

26. The method according to claim 25, wherein the structure of the nucleic acid delivery system is a matrix or a microsphere.

27. The method according to claim 25, wherein the biocompatible polymer is poly(ethylene-co-vinyl acetate), poly(lactide-co-glycolide), poly(caprolactone), poly(lactide), polyglycolide, polyanhydride, polyorthoester, polyphosphazene, proteinaceous polymer, polyester, silicone, or combinations thereof.

28. The method according to claim 25, wherein the one or more nucleic acid molecules are the same or different with each being inserted in a heterologous expression vector.

29. The method according to claim 25, wherein each of the one or more nucleic acid molecules is a DNA molecule, the nucleic acid delivery system further comprising:
a nucleus translocation polypeptide coupled individually to each DNA molecule.

30. The method according to claim 25, wherein the mixture further comprises a cellular uptake agent.

31. The method according to claim 30, wherein the cellular uptake agent is coupled individually to each of the one or more nucleic acid molecules.

32. The method according to claim 25, wherein the mixture further comprises:
a second co-dispersant selected from the group consisting of a cationic polymer, a DNA binding protein, and a DNase inhibitor.

33. The method according to claim 25, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes.

34. The method according to claim 33, wherein said administering is carried out by implanting the nucleic acid delivery system in the patient.

35. The method according to claim 34, wherein said implanting is carried out by implanting the nucleic acid delivery system in a tissue comprising the cell.

36. The method according to claim 33, wherein said administering is carried out by injecting the nucleic acid delivery system into the patient.

37. The method according to claim 25, wherein the nucleic acid delivery system is present in the form of a composition comprising the nucleic acid delivery system and a pharmaceutically-acceptable carrier and said administering is carried out by administering the composition into the patient.

38. The method according to claim 25, wherein the one or more nucleic acid molecules each encode a protein or polypeptide.

39. The nucleic acid delivery system according to claim 1, wherein the weight ratio of the one or more nucleic acid molecules to the first co-dispersant is about 0.0001–1:1.

40. A method of making a nucleic acid delivery system comprising:
providing a mixture comprising one or more nucleic acid molecules and a first co-dispersant, which is an inert polymer that does not interact with the one or more nucleic acid molecules;
providing a biocompatible polymer that is different from the inert polymer; and
combining the mixture with the biocompatible polymer under conditions effective to form a polymeric structure in which the mixture is contained, wherein the first co-dispersant is present in an amount that is effective to reduce the rate of diffusion of the one or more nucleic acid molecules from the polymeric structure as compared to a polymeric structure comprising the one or more nucleic acid molecules absent an effective amount of the first co-dispersant.

41. The method according to claim 40, wherein said providing a biocompatible polymer comprises:
providing the biocompatible polymer dissolved in a solvent to form a solution.

42. The method according to claim 41, wherein the biocompatible polymer is poly(ethylene-co-vinyl acetate), poly(lactide-co-glycolide) or poly(lactic acid) and the solvent is methylene chloride.

43. The method according to claim 41, wherein said combining is carried out by
substantially mixing the mixture into the solution;
introducing the solution into a mold; and
treating the solution under conditions effective substantially to remove the solvent, thereby yielding the polymeric structure in which the mixture is contained.

44. The method according to claim 41, wherein said providing the mixture comprises:
dissolving the mixture in a second solvent to produce a second solution.

45. The method according to claim 44, wherein said combining is carried out by
blending the solution and the second solution under conditions effective to form a first emulsion;
introducing polyvinyl alcohol to the first emulsion under conditions effective to form a second emulsion; and treating the second emulsion under conditions effective to form the polymeric structure in which the mixture is contained.

46. A nucleic acid delivery system comprising:
a polymeric structure formed of a biocompatible polymer and
a mixture comprising (i) one or more nucleic acid molecules that encode a protein or polypeptide or RNA product, and (ii) a first co-dispersant that is inert with respect to the one or more nucleic acid molecules and is selected from the group consisting of herring sperm DNA, a random or non-coding DNA having a molecular weight of about 100 kDa to about 2000 kDa, a DNase-free filler, a DNase-free bulk protein, Ficoll, dextran, diethylaminoethyl-dextran, dextran sulfate, ovalbumin, DNase free peptide, glycoproteins, peptide-nucleic acids, and combinations thereof, the mixture being contained within the polymeric structure, wherein the first co-dispersant is present in an amount effective to reduce the rate of diffusion of the one or more nucleic acid molecules from the polymeric structure.

47. A method of inducing an immune response in a patient comprising:
providing a nucleic acid delivery system according to claim 46, wherein the one or more nucleic acid molecules encode an antigenic protein or polypeptide; and
administering the nucleic acid delivery system to a patient under conditions effective to cause sustained release of the one or more nucleic acid molecules from the nucleic acid delivery system and uptake of the one or more nucleic acid molecules by cells of the patient, whereby upon expression of the one or more nucleic acid molecules the antigenic protein or polypeptide is expressed and an immune response is induced against the antigenic protein or polypeptide.

* * * * *